US006413726B1

(12) United States Patent
Ni et al.

(10) Patent No.: US 6,413,726 B1
(45) Date of Patent: Jul. 2, 2002

(54) ANTIBODIES THAT SPECIFICALLY BIND CYTOSTATIN III

(75) Inventors: Jian Ni, Rockville; Guo-Liang Yu, Darnestown; Reiner Gentz, Silver Spring; Patrick J. Dillon, Gaithersburg, all of MD (US)

(73) Assignee: Human Genome Sciences, Inc., Rockville, MD (US)

(*) Notice: Subject to any disclaimer, the term of this patent is extended or adjusted under 35 U.S.C. 154(b) by 0 days.

(21) Appl. No.: 09/734,036

(22) Filed: Dec. 12, 2000

Related U.S. Application Data

(62) Division of application No. 09/307,817, filed on May 10, 1999, now Pat. No. 6,232,291, which is a division of application No. 08/820,825, filed on Mar. 19, 1997, now Pat. No. 5,945,309.
(60) Provisional application No. 60/013,655, filed on Mar. 19, 1996.

(51) Int. Cl.⁷ .......................... G01N 33/50; C07K 16/00
(52) U.S. Cl. .................. 435/7.1; 435/326; 435/327; 435/328; 435/331; 435/335; 435/346; 435/336; 424/130.1; 424/131.1; 424/133.1; 424/139.1; 424/141.1; 424/142.1; 424/145.1; 424/158.1; 424/178.1; 530/387.1; 530/387.2; 530/387.3; 530/387.9; 530/388.1; 530/388.15; 530/358.23; 530/388.24; 530/389.1; 530/389.2; 530/391.3
(58) Field of Search ................... 530/387.1, 387.2, 530/387.3, 387.9, 388.1, 388.15, 388.23, 388.24, 389.1, 389.2, 391.3; 424/130.1, 131.1, 133.1, 139.1, 141.1, 142.1, 145.1, 158.1, 178.1; 435/326, 327, 328, 331, 335, 336, 346, 7.1

(56) References Cited

U.S. PATENT DOCUMENTS 5,945,309 A 8/1999 Ni et al.
6,046,027 A 4/2000 Bandman et al.
6,232,291 B1 * 5/2001 Ni et al.

OTHER PUBLICATIONS

Huynh et al., "Tumor Suppressor Activity of the Gene Encoding Mammary–derived Growth Inhibitor," *Cancer Research*, 55:2225–2231 (Jun. 1, 1995).
Phelan et al., "The Human Mammary–Derived Growth Inhibitor (MDGI) Gene: Genomic Structure and Mutation Analysis in Human Breast Tumors," *Genomics*, 34:63–68 (1996).
Sherman et al., "Rat cellular retinol–binding protein: cDNA sequence and rapid retinol–dependent accumulation of mRNA," *PNAS (USA)*, 84:3209–3213 (May 1987).
Bowie et al., "Deciphering the Message in Protein Sequences: Tolerance to Amino Acid Substitutions," *Science*, 247:1306–1310 (1990).
Wells, "Additivity of Mutational Effects in Proteins," *Biochem.*, 29(37):8509–8517 (1990).
Ngo et al., "Computational Complexity, Protein Structure Prediction, and the Levinthal Paradox," The Protein Folding Problem and Tertiary Structure Prediction, Merz et al., eds., Birkhauser, Boston pp. 433–506 (1994).
Schulz et al., "Principles of Protein Structure," Springer–Verlag, New York pp. 14–16 (1979).

* cited by examiner

*Primary Examiner*—Elizabeth Kemmerer
(74) *Attorney, Agent, or Firm*—Human Genome Sciences, Inc.

(57) ABSTRACT

The invention relates to Cytostatin III polypeptides, polynucleotides encoding the polypeptides, methods for producing the polypeptides, in particular by expressing the polynucleotides, and agonists and antagonists of the polypeptides. The invention further relates to methods for utilizing such polynucleotides, polypeptides, agonists and antagonists for applications, which relate, in part, to research, diagnostic and clinical arts.

70 Claims, 3 Drawing Sheets

```
                10                  30                  50
CACGAGCTGGAATCTCTCAGCCTCACCTGCCAGACAACACCCCCTCCTTCCTCACCCTGT
                70                  90                 110
CTCCTGCATTCTCCTGAAACCTTCATCCACACAATGCCTCCCAACCTCACTGGCTACTAC
                                          M  P  P  N  L  T  G  Y  Y
               130                 150                 170
CGCTTTGTCTCGCAGAAGAACATGGAGGACTACCTGCAAGCCCTAAACATCAGCTTGGCT
 R  F  V  S  Q  K  N  M  E  D  Y  L  Q  A  L  N  I  S  L  A
               190                 210                 230
GTGCGGAAGATCGCGCTGCTGCTGAAGCCGGACAAGGAGATCGACACCAGGGCAACCAC
 V  R  K  I  A  L  L  L  K  P  D  K  E  I  E  H  Q  G  N  H
               250                 270                 290
ATGACGGTGAGGACGCTCAGCACCTTCCGAAACTACACTTTGCAGTTTGATGTGGGAGTG
 M  T  V  R  T  L  S  T  F  R  N  Y  T  L  Q  F  D  V  G  V
               310                 330                 350
GAGTTTGAGGAGGACCTCAGGAGCGTGGACGGACGAAAATGCCAGACCATAGTAACCTGG
 E  F  E  E  D  L  R  S  V  D  G  R  K  C  Q  T  I  V  T  W
               370                 390                 410
GAGGAGGAGCACCTGGTGTGTGTGCAGAAAGGGGAGGTCCCCAACCGGGGCTGGAGACAC
 E  E  E  H  L  V  C  V  Q  K  G  E  V  P  N  R  G  W  R  H
               430                 450                 470
TGGCTGGAGGGAGAGATGCTGTATCTGGAACTGACTGCAAGGGATGCAGTGTGCGAGCAG
 W  L  E  G  E  M  L  Y  L  E  L  T  A  R  D  A  V  C  E  Q
               490                 510                 530
GTCTTCAGGAAGGTCAGATAGCCGGAGAGGAGCCAAGATCCCTCCAGACAGCACCAGCTC
 V  F  R  K  V  R  *
               550                 570                 590
ACAGACGCTCTTGTTGTGCCCCCTTCAAGCCCAGATTGTGCCAGGTCAGCTGTCCCTTCC
               610                 630                 650
TCTGGCCACCTTTCCTCCCTCTGGGTCCCTCCTCACCCCTCCCCGTGTTAATCTGTAACT
               670                 690                 710
TGGAGCCCCCAGGACAAAGTCCTTTCTCACACTCCACTGCCCAATAGTGACCTCACTTCC
               730                 750                 770
AGGTCAAGGTCTGGCGTCCCAAATGAAAGAAGCAGGCAAAGGGAAGGAGCCCCTGAGGAC
               790                 810                 830
AACCAATCTCCGCTCTCTCCTGTCCATTTGACCTCTTCTTTTCCTTCTAAGAAAGAACTA
               850                 870                 890
AGCTTTGGGCATTTGGCGATTAGTGAAAATTCTATCCTGATGGACTTCTGGAAAACTGTG
               910                 930
ACTGGGGTTCAACAGTTTAAACAGGGGCTACTGGGGGAAAAAAA
```

FIG.1

```
       M V D A F V G T W K L V D S K N F D D Y M K A L G V G F A T    Majority
                        10                  20                  30
  1    M A D A F V G T W K L V D S K N F D D Y M K S L G V G F A T    Mouse MDGI
  1    M V D A F V G T W K L V D S K N F D D Y M K S L G V G F A T    Bovine MDGI
  1    M V D A F L G T W K L V D S K N F D D Y M K S L G V G F A T    Human MDGI
  1    M P P N L T G Y Y R F V S Q K N M E D Y L Q A L N I S L A V    Cytostatin I
  1    M V E A F C A T W K L T N S Q N F D E Y M K A L G V G F A T    Cytostatin II
  1    M P P N L T G Y Y R F V S Q K N M E D Y L Q A L N I S L A V    Cytostatin III R Q V A L M T K P T T I I E K N G D T V T I K T L S T F K N    Majority
                        40                  50                  60
 31    R Q V A S M T K P T T I I E K N G D T I T I K T Q S T F K N    Mouse MDGI
 31    R Q V G N M T K P T T I I E V N G D T V I I K T Q S T F K N    Bovine MDGI
 31    R Q V A S M T K P T T I I E K N G D I L T L K T H S T F K N    Human MDGI
 31    R K I A L L K P D K E I E H Q G N H M T V R T L S T F R N      Cytostatin I
 31    R Q V G N V T K P T V I I S Q E G D K V V I R T L S T F K N    Cytostatin II
 31    R K I A L L K P D K E I E H Q G N H M T V R T L S T F R N      Cytostatin III T E I S F D L G V E F D E T - - T A D D R K V K S I V T L D    Majority
                        70                  80                  90
 61    T E I N F Q L G I E F D E V - - T A D D R K V K S L V T L D    Mouse MDGI
 61    T E I S F K L G V E F D E T - - T A D D R K V K S I V T L D    Bovine MDGI
 61    T E I S F K L G V E F D E T - - T A D D R K V K S I V T L D    Human MDGI
 61    Y T L Q F D V G - - - - - - - - - - - - - - - - - - - - -      Cytostatin I
 61    T E I S F Q L G E E F D E T - - T A D D R N C K S V V S L D    Cytostatin II
 61    Y T L Q F D V G V E F E E D L R S V D G R K C Q T I V T W E    Cytostatin III G G K L V H V Q K W D G Q E T N L V R E - - - - L V D G K L    Majority
                       100                 110                 120
 89    G G K L I H V Q K W N G Q E T T L T R E - - - - L V D G K L    Mouse MDGI
 89    G G K L V H V Q K W N G Q E T S L V R E - - - - M V D G K L    Bovine MDGI
 89    G G K L V H L Q K W D G Q E T T L V R E - - - - L I D G K L    Human MDGI
 89    - - - - - - V Q K - - G E V P N - - R G W R H W L E G E L L    Cytostatin I
 89    G D K L V H I Q K W D G K E T N F V R E - - - - I K D G K M    Cytostatin II
 91    E E H L V C V Q K - - G E V P N - - R G W R H W L E G E M L    Cytostatin III I L T L T H G D A V C T R T Y E K V - X                        Majority
                       130                 140
115    I L T L T H G S V V S T R T Y E K E - A                        Mouse MDGI
115    I L T L T H G T A V C T R T Y E K Q - A                        Bovine MDGI
115    I L T L T H G T A V C T R T Y E K E - A                        Human MDGI
 89    Y L E L T A R D A V C E Q V F R K V R                          Cytostatin I
115    V M T L T F G D V A V R H Y E K A -                            Cytostatin II
117    Y L E L T A R D A V C E Q V F R K V R                          Cytostatin III
```

FIG.2

ANTIBODIES THAT SPECIFICALLY BIND CYTOSTATIN III

This application is a divisional of U.S. application Ser. No. 09/307,817, filed May 10, 1999, now U.S. Pat. No. 6,232,291, which is a divisional of and claims priority to U.S. application Ser. No. 08/820,825, filed Mar. 19, 1997, now issued as U.S. Pat. No. 5,945,309, which claims benefit of Provisional Application No. 60/013,655, filed Mar. 19, 1996, all of which are hereby incorporated by reference.

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of human Cytostatin III.

BACKGROUND OF THE INVENTION

The growth and differentiation of cells and the development of tissues and glands is controlled by autocrine and paracrine factors, such as systemic hormones and factors that modulate or mediate the action of hormones, such as growth factors, which themselves may be hormones.

For example, peptides that locally signal growth cessation and stimulate differentiation of cells of the developing epithelium are very important to mammary gland development. These factors largely have not been identified or characterized, particularly not in humans.

A few factors that play a role in the humoral mediation of growth and differentiation of cells in tissues and glands, mammary glands in particular, have been identified in non-human organisms. One such factor is mammary-derived growth inhibitor ("MDGI"). (Grosse et al., 5. Mammary-Derived Growth Inhibitor (MDGI) in GENES, ONCOGENES, AND HORMONES: ADVANCES IN CELLULAR AND MOLECULAR BIOLOGY OF BREAST CANCER, Dickson et al., Eds., Kluwer Academic Publishers, Boston (1991)). MDGI was first identified in milk and mammary glands of cows. Subsequently, it was identified in mice. In mice and cows, at least, MDGI has been shown to inhibit epithelial cell growth and stimulate epithelial cell differentiation.

MDGI occurs in at least two forms produced by alternative routes of post-translational processing. The original form is referred to as MDGI and the second form is called MDGI-2.

MDGI is associated primarily with milk fat globule membranes ("MFGM"), as assessed by immnunological assays using anti-MDGI antibodies. Similar time course studies show that MDGI increases dramatically in mammary glands when lactation begins, following delivery. MDGI-2 differs from MDGI in this respect. It is found in mammary glands during pregnancy but not during lactation. (Grosse et al. cited above and Kurtz et al. J. Cell. Biol. 110: 1779–1789 (1990))

The roles of the two forms of MDGI and their mechanism(s) of action are not clearly defined. Mouse and bovine MDGI are homologous to one another and to a family of low molecular mass hydrophobic ligand-binding proteins ("low MW HLBP(s)"), which includes fatty acid-binding proteins ("FABP(s)") from brain, heart, liver and intestine, myelin P2 protein, the differentiation associated protein of adipocytes called p422 gastrotropin and cellular retinoic acid-binding protein ("CRABP"). These proteins which bind hydrophobic ligands such as long-chain fatty acids, retinoids and eiconsanoids and they are thought to play roles in the transport, sequestration, or metabolism of fatty acids and fatty acid derivatives. However, they are expressed in a differentiation specific manner, in cells of the mammary gland, heart, liver, brain and intestine, and they appear not only to play roles in basal metabolism but also to play important roles in differentiation and development.

The homology of MDGI to the low MW HLBPs raises the possibility that MDGI, at least as part of its function, binds a hydrophobic ligand, and that binding to this ligand is important to the mechanism(s) by which MDGI inhibits cell growth and stimulates differentiation. It should be noted, however, that the other low MW HLBPs, except gastrotropin, act intracellularly, whereas MDGI acts extracellularly, at least in vitro. (Yang et al., J. Cell Biol. 127: 1097–1109 (1994).

Among the low MW HLBPs, MDGI most closely resembles the fatty acid binding proteins ("FABP"). FABPs have been identified in brain, heart, liver and intestine. Heart FABP, like MDGI, whether produced from natural sources or by expression of a cloned gene in a heterologous host, inhibits growth of normal mammary epithelial cells ("MEC") of mouse origin. In addition, it stimulates milk protein synthesis and it stimulates its own expression in these cells. However, unlike bovine heart FABP, bovine MDGI does not bind fatty acids, although the two proteins are 95% homologous and it has been suggested that heart FABP actually may be a form of MDGI. (Treuner et al., Gene 147: 237–242 (1994)) Thus, even if MDGI is a low MW HLBP, its substrate affinities are distinct from its close relatives in the family, and it therefore likely plays a different physiological role.

In vivo MDGI is found in capillary endothelial cells and in the mammary parenchyma, in mice and cows. (See, for instance, Grosse et al. cited above.) MDGI appears first in the capillary endothelial cells and later in the secretory epithelial cells. The location of MDGI in the mammary capillary endothelium is consistent with a role in regulating endothelial cell proliferation.

A number of activities of MDGI have been demonstrated in vitro, as discussed in Grosse et al. cited above, for example. For instance, it has been shown that MDGI inhibits L(+)-lactate-, arachidonic acid- and 15-S-hydroxyeicosatetraenoic acid-induced supersensitivity of neonatal rat heart cells to beta-adrenergic stimulation. As reported by Burton et al., BBRC 205: 1822–1828 (1994), the induced hypersensitivity is mediated by a small population of beta 2-adrenergic receptors and, therefore, it has been suggested that MDGI interferes with the normal function of these receptors. Interaction with these receptors might also be part of the mechanism by which MDGI inhibits cells growth. This activity also raises the possibility that MDGI naturally modulates the beta-adrenergic sensitivity of cardiac myocytes.

Furthermore, as reported by Burton et al. cited above, H-FABP can be a potent inducer of cardiac myotrophy, capable of stimulating protein synthesis and c-jun expression in myocytes, and increasing their surface area. The effect of MDGI on differentiation of mammary epithelial cells ("MEC") has been further demonstrated by antisense inhibition experiments using phosphorothioate oligonucleotides. (Yang at al. cited above.) These experiments show that MDGI antisense molecules decrease beta-casein levels and suppress the appearance of alveolar end buds in organ cultures. Furthermore, MDGI suppresses the mitogenic effects of epidermal growth factor, and epidermal growth factor antagonizes the activities of MDGI. MDGI is the first known growth inhibitor which promotes mammary gland differentiation.

The regulatory properties of MDGI can be fully mimicked by an 11-amino acid sequence, which is represented in the carboxyl terminus of MDGI and a subfamily of the low MW HLBPs.

Not all mammary epithelial cell lines respond to MDGI in the same way. MDGF inhibits growth of normal human MEC, passaged for varying lengths of time. (Yang et al. cited above.) It also inhibits growth of the mouse mammary malignant epithelial cell lines mMaCa 20177, the human malignant mammary cell lines MaTu and T47D and it inhibits the resumption of growth of stationary Ehrlich ascites carcinoma cells ("EAC") in vitro. In contrast, MDGF slightly stimulates growth of the human malignant mammary epithelial cell line MCF7. Finally, MDGI promotes differentiation of mouse pluripotent embryonic stem cells.

The mechanism of the effects of MDGI on cells is not known, as yet. The resumption of growth of stationary Ehrlich ascites carcinoma cells ("EAC") in vitro is accompanied by a rapid increase in cellular c-fos, c-myc and c-ras mRNA. The rapid induction of these genes upon exposure to MDGI underscores the importance of oncogene expression to growth regulation and evidences a positive correlation between cell growth and expression of c-fos, c-myc and c-ras. Furthermore, the effect of MDGI on expression of these genes indicates that it is a positive effector of cellular protooncogene expression, either directly or through one or more signaling pathways, or both.

It also has been shown that MDGI can function as a potent tumor suppressor gene. (Huynh et al., Caner Res., 55: 2225 (1995)) Human breast cancer cells transfected with an MDGI expression construct exhibited differentiated morphology, reduced proliferation rate, reduced clonogenicity in soft agar, and reduced tumorgenicity in nude mice. The human homologue of this gene was mapped to chromosome 1p33-35, a locus previously shown to exhibit frequent loss of heterozygosity in human breast cancer (about 40% of tumors). The magnitude of the in vivo and in vitro tumor suppressor activity of MDGI is comparable to that previously observed for BRCA1, p53, Rb, and H19.

The effects of MDGF on cell growth and differentiation, and on cellular protooncogene expression reiterate the importance of soluble factors in normal growth and differentiation of cells, tissues, glands and organs, and their roles in aberrant cell growth, dysfunction and disease. Clearly, there is a need for factors that regulate growth and differentiation of normal and abnormal cells. There is a need, therefore, for identification and characterization of such factors that modulate growth and differentiation of cells, both normally and in disease states. In particular, there is a need to isolate and characterize additional cytostatins akin to MDGI that modulate growth and differentiation of cells, such as epithelial cells, particularly mammary epithelial cells, are essential to the proper development and health of tissue and organs, such as mammary glands of developing and adult females, particularly human females, and, among other things, can play a role in preventing, ameliorating or correcting dysfunctions or diseases.

SUMMARY OF THE INVENTION

Toward these ends, and others, it is an object of the present invention to provide polypeptides, inter alia, that have been identified as novel cytostatins by homology between the amino acid sequence set out in FIG. 1 (SEQ ID NO:2) and known amino acid sequences of other proteins such as MDGI proteins.

It is a further object of the invention, moreover, to provide polynucleotides that encode cytostatins, particularly polynucleotides that encode the polypeptide herein designated Cytostatin III.

In a particularly preferred embodiment of this aspect of the invention the polynucleotide comprises the region encoding human Cytostatin III in the sequence set out in FIG. 1 (SEQ ID NO:2).

In accordance with this aspect of the present invention there is provided an isolated nucleic acid molecule encoding a mature polypeptide expressed by the human cDNA contained in ATCC Deposit No. 97332.

In accordance with this aspect of the invention there are provided isolated nucleic acid molecules encoding human Cytostatin III, including mRNAs, cDNAs, genomic DNAs and, in further embodiments of this aspect of the invention, biologically, diagnostically, clinically or therapeutically useful variants, analogs or derivatives thereof, or fragments thereof, including fragments of the variants, analogs and derivatives. Among the particularly preferred embodiments of this aspect of the invention are naturally occurring allelic variants of human Cytostatin III.

It also is an object of the invention to provide Cytostatin III polypeptides, particularly human Cytostatin III polypeptides, that modulate growth activity of epithelial cells, stimulate milk production in both humans and cows and promote involution of the breast.

In accordance with this aspect of the invention there are provided novel polypeptides of human origin referred to herein as Cytostatin III as well as biologically, diagnostically or therapeutically useful fragments, variants and derivatives thereof, variants and derivatives of the fragments, and analogs of the foregoing. Among the particularly preferred embodiments of this aspect of the invention are variants of human Cytostatin III encoded by naturally occurring alleles of the human Cytostatin III gene.

It is another object of the invention to provide a process for producing the aforementioned polypeptides, polypeptide fragments, variants and derivatives, fragments of the variants and derivatives, and analogs of the foregoing.

In a preferred embodiment of this aspect of the invention there are provided methods for producing the aforementioned Cytostatin III polypeptides comprising culturing host cells having expressibly incorporated therein an exogenously-derived human Cytostatin III-encoding polynucleotide under conditions for expression of human Cytostatin III in the host and then recovering the expressed polypeptide.

In accordance with another object the invention there are provided products, compositions, processes and methods that utilize the aforementioned polypeptides and polynucleotides for research, biological, clinical and therapeutic purposes, inter alia. In accordance with certain preferred embodiments of this aspect of the invention, there are provided products, compositions and methods, inter alia, for, among other things: assessing Cytostatin III expression in cells by determining Cytostatin III polypeptides or Cytostatin III-encoding mRNA; modulating cell growth in vitro, ex vivo or in vivo by exposing cells to Cytostatin III polypeptides or polynucleotides as disclosed herein; assaying genetic variation and aberrations, such as defects, in Cytostatin III genes; and administering a Cytostatin III polypeptide or polynucleotide to an organism to augment Cytostatin III function or remediate Cytostatin III dysfunction.

In accordance with certain preferred embodiments of this and other aspects of the invention there are provided probes that hybridize to human Cytostatin III sequences. In certain additional preferred embodiments of this aspect of the invention there are provided antibodies against Cytostatin III polypeptides. In certain particularly preferred embodiments in this regard, the antibodies are highly selective for human Cytostatin III. In accordance with another aspect of the present invention, there are provided Cytostatin III agonists. Among preferred agonists are molecules that mimic Cytostatin III, that bind to Cytostatin III-binding molecules or receptor molecules, and that elicit or augment Cytostatin III-induced responses. Also among preferred agonists are molecules that interact with Cytostatin III or Cytostatin III polypeptides, or with other modulators of Cytostatin III activities, and thereby potentiate or augment an effect of Cytostatin III or more than one effect of Cytostatin III.

In accordance with yet another aspect of the present invention, there are provided Cytostatin III antagonists. Among preferred antagonists are those which mimic Cytostatin III so as to bind to Cytostatin III receptor or binding molecules but not elicit a Cytostatin III-induced response or more than one Cytostatin III-induced response. Also among preferred antagonists are molecules that bind to or interact with Cytostatin III so as to inhibit an effect of Cytostatin III or more than one effect of Cytostatin III or which prevent expression of Cytostatin III.

The agonists and antagonists may be used to mimic, augment or inhibit the action of Cytostatin III polypeptides. They may be used, for instance, for purposes relating to growth of cells in vitro or for purposes relating to treatment of disorders associated with aberrant growth of cells affected by cytostatins, particularly Cytostatin III.

In a further aspect of the invention there are provided compositions comprising a Cytostatin III polynucleotide or a Cytostatin III polypeptide for administration to cells in vitro, to cells ex vivo and to cells in vivo, or to a multicellular organism. In certain particularly preferred embodiments of this aspect of the invention, the compositions comprise a Cytostatin III polynucleotide for expression of a Cytostatin III polypeptide in a host organism for treatment of disease. Particularly preferred in this regard is expression in a human patient for treatment of a dysfunction associated with aberrant endogenous activity of Cytostatin III.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIG. 1 shows the nucleotide (SEQ ID NO:1) and deduced amino acid sequence (SEQ ID NO:2) of human Cytostatin III.

FIG. 2 shows the regions of similarity between amino acid sequences of cytostatin and MDGI polypeptides (SEQ ID NO:11–15 and 2, respectively).

GLOSSARY

Figure 3:
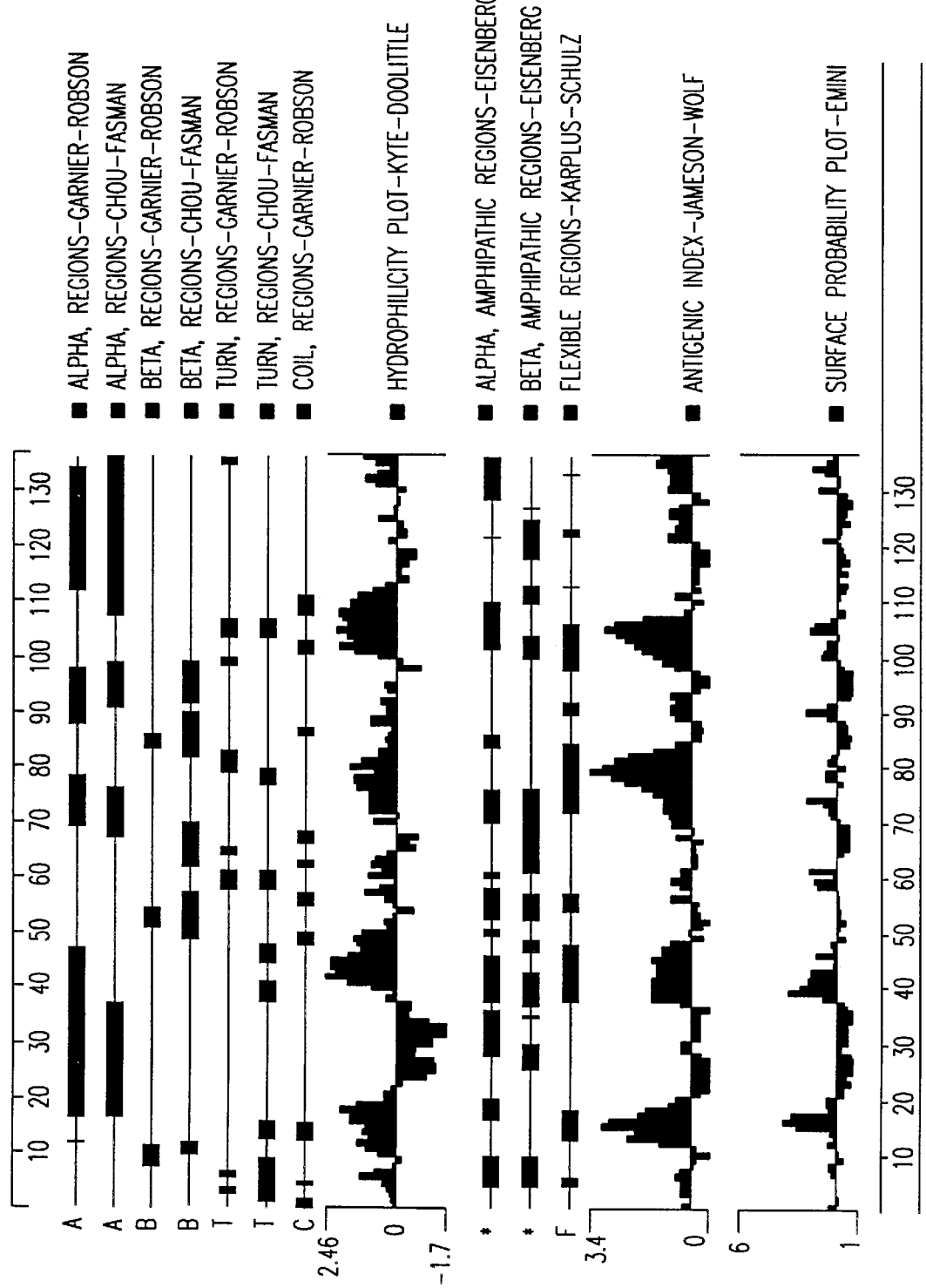
FIG. 3 shows structural and functional features of Cytostatin III deduced by the indicated techniques, as a function of amino acid sequence.

The following illustrative explanations are provided to facilitate understanding of certain terms used frequently herein, particularly in the examples. The explanations are provided as a convenience and are not limitative of the invention.

DIGESTION of DNA refers to catalytic cleavage of the DNA with a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 mg of plasmid or DNA fragment is digested with about 2 units of enzyme in about 20 ml of reaction buffer. For the purpose of isolating DNA fragments for plasmid construction, typically 5 to 50 mg of DNA are digested with 20 to 250 units of enzyme in proportionately larger volumes. Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

GENETIC ELEMENT generally means a polynucleotide comprising a region that encodes a polypeptide or a region that regulates transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome; not in their natural state but, rather, following manipulation such as isolation, cloning and introduction into a host cell in the form of purified DNA or in a vector, among others.

ISOLATED means altered from "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulations, solutions for introduction of polynucleotides or polypeptides, for example, into cells, compositions or solutions for chemical or enzymatic reactions, for instance, which are not naturally occurring compositions, arid, therein remain isolated polynucleotides or polypeptides within the meaning of that term as it is employed herein.

LIGATION refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989) and Maniatis et al., pg. 146, as cited below. OLIGONUCLEOTIDE(S) refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, readily will form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation. PLASMIDS generally are designated herein by a lower case p preceded and/or followed by capital letters and/or numbers, in accordance with standard naming conventions that are familiar to those of skill in the art.

Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

POLYNUCLEOTIDE(S) generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single-and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

POLYPEPTIDES, as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides, as is well known and as the term is used herein, generally are formed of the 20 naturally occurring amino acids, and that the amino acids in a polypeptide generally are joined to one another in a linear chain by peptide bonds between the alpha carboxyl and the alpha amino groups of adjacent, succeeding amino acids.

By convention, the sequence of amino acids in a chain usually, but not always, is written beginning (on the left and at the top) with the amino acid having a free alpha amino group. This amino acid is taken as the amino terminus of the polypeptide, also referred to as the N-terminus. Each successive amino acid then is listed in turn, ending with the amino acid having a free carboxyl group (at bottom and right), which is taken as the carboxyl terminus of the polypeptide, also called the C-terminus.

Individual amino acids in a polypeptide commonly are referred to as amino acid residues, and as residues.

Generally, the amino acids in a polypeptide are numbered beginning with the amino terminus and proceeding integer by integer and residue by residue to the carboxyl terminus. However, for polypeptides that first are synthesized in cells as precursors to a mature form, it also is common to begin numbering amino acids with the first residue of the mature form. Then, the upstream residues (i.e., those closer to the N-terminus) are assigned negative numbers counting back from residue one (the N-terminus of the mature form) to the N-terminus of the earliest precursor form. Other numbering schemes also have been employed, but less commonly.

Notwithstanding the foregoing general characteristics, it will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art.

Among the known modifications which may be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York (1983); Seifter et al., Analysis for protein modifications and nonprotein cofactors, Meth. Enzymol. 182: 626–646 (1990) and Rattan et al., Protein Synthesis: Posttranslational Modifications and Aging, Ann. N.Y. Acad. Sci. 663: 48–62 (1992).

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cell often carry out the same post-translational glycosylations as mammalian cells and, for this reason, insect cell expression systems have been developed to express efficiently mammalian proteins having native patterns of glycosylation, inter alia. Similar considerations apply to other modifications.

It will be appreciated that the same type of modification may be present in the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

VARIANT(S) of polynucleotides or polypeptides, as the term is used herein, are polynucleotides or polypeptides that differ from a reference polynucleotide or polypeptide, respectively. Variants in this sense are described below and elsewhere in the present disclosure in greater detail.

A polynucleotide that differs in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

A polypeptide that differs in amino acid sequence from another, reference polypeptide. Generally, differences are limited so that the sequences of the reference and the variant are closely similar overall and, in many region, identical.

A variant and reference polypeptide may differ in amino acid sequence by one or more substitutions, additions, deletions, fusions and truncations, which may be present in any combination.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

RECEPTOR MOLECULE, as used herein, refers to molecules which bind or interact specifically with Cytostatin III polypeptides of the present invention, including not only classic receptors, which are preferred, but also other molecules that specifically bind to or interact with polypeptides of the invention (which also may be referred to as "binding molecules" and "interaction molecules," respectively and as "Cytostatin III binding molecules" and "Cytostatin III interaction molecules." Binding between polypeptides of the invention and such molecules, including receptor or binding or interaction molecules may be exclusive to polypeptides of the invention, which is very highly preferred, or it may be highly specific for polypeptides of the invention, which is highly preferred, or it may be highly specific to a group of proteins that includes polypeptides of the invention, which is preferred, or it may be specific to several groups of proteins at least one of which includes polypeptides of the invention.

Such molecules generally are proteins, which may be single or multichain proteins and multisubunit or multiprotein complexes, such as those of classic cell surface receptors, which are highly preferred in the invention. Receptor molecules also may be non-protein molecules that bind to or interact specifically with polypeptides of the invention.

Such molecules may occur in membranes, such as classic cell surface receptors, or they may occur intracellularly, in the cytosol, inside organelles, or in the surface of organelles, for instance. Among particularly preferred receptor molecules in this regard are membrane bound receptors, particularly cell membrane receptors, especially cell surface receptors. Also among preferred receptors are those that occur in the membranes of organelles, particularly nuclear membrane receptors and mitochondrial membrane receptors.

Receptors also may be non-naturally occurring, such as antibodies and antibody-derived reagents that bind specifically to polypeptides of the invention.

DESCRIPTION OF THE INVENTION

The present invention relates to novel Cytostatin III polypeptides and polynucleotides, among other things, as described in greater detail below. In particular, the invention relates to polypeptides and polynucleotides of a novel human Cytostatin III, which is related by amino acid sequence homology to the mammary derived growth inhibitor ("MDGF") found in cows and mice. The invention relates especially to Cytostatin III having the nucleotide and amino acid sequences set out in FIG. 1 (SEQ ID NO:1 and 2), and to the Cytostatin III nucleotide and amino acid sequences of the cDNA in ATCC Deposit No. 97332 which is herein referred to as "the deposited clone" or as the "cDNA of the deposited clone." It will be appreciated that the nucleotide and amino acid sequences set out in FIG. 1 (SEQ ID NO:1 and 2) were obtained by sequencing the human cDNA of the deposited clone. Hence, the sequence of the deposited clone is controlling as to any discrepancies between the two and any reference to the sequences of FIG. 1 (SEQ ID NO:1) include reference to the sequence of the human cDNA of the deposited clone.

Polynucleotides

In accordance with one aspect of the present invention, there are provided isolated polynucleotides which encode the Cytostatin III polypeptide having the deduced amino acid sequence of FIG. 1 (SEQ ID NO:2).

Using the information provided herein, such as the polynucleotide sequence set out in FIG. 1 (SEQ ID NO:1), a polynucleotide of the present invention encoding human Cytostatin III polypeptide may be obtained using standard cloning and screening procedures, such as those for cloning cDNAs using MRNA from cells of a breast lymph node as starting material. Illustrative of the invention, the polynucleotide set out in FIG. 1 (SEQ ID NO:1) was discovered in a cDNA library derived from cells of a human breast lymph node.

Human Cytostatin III of the invention is structurally related to other proteins of the cytostatin family of growth modulating factors, as shown by the results of sequencing the cDNA encoding human Cytostatin III in the deposited clone. The human cDNA sequence thus obtained is set out in FIG. 1 (SEQ ID NO:1). It contains an open reading frame encoding a protein of about 135 amino acid residues with a deduced molecular weight of about 15.9 kDa. The protein exhibits greatest homology to mouse mammary-derived growth inhibitor ("MDGI"), among known proteins. The first 133 residues of the Cytostatin III of FIG. 1 (SEQ ID NO:2) have about 33% identity and about 62% similarity with the amino acid sequence of mouse MDGI.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand.

A polynucleotide of the present invention may a naturally occurring sequence, such as that of a naturally occurring allelic variant, or it may have a sequence that does not occur in nature, such as a sequence that has been produced, for instance, by in vitro mutagenesis techniques.

The coding sequence which encodes the polypeptide may be identical to the coding sequence of the polynucleotide shown in FIG. 1 (SEQ ID NO:1). It also may be a polynucleotide with a different sequence, which, as a result of the redundancy (degeneracy) of the genetic code, encodes the polypeptide of the DNA of FIG. 1 (SEQ ID NO:1).

Polynucleotides of the present invention which encode the polypeptide of FIG. 1 (SEQ ID NO:2) may include, but are not limited to the coding sequence for the mature polypeptide, by itself, the coding sequence for the mature polypeptide and additional coding sequences, such as those encoding a leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing—including splicing and polyadenylation signals, for example—ribosome binding and stability of mRNA.

In accordance with the foregoing, the term "polynucleotide encoding a polypeptide" as used herein encompasses polynucleotides which include a sequence encoding a polypeptide of the present invention, particularly the human Cytostatin III having the amino acid sequence set out in FIG. 1 (SEQ ID NO:2). The term encompasses polynucleotides that include a single continuous region or discontinuous regions encoding the polypeptide, together with additional regions, that also may contain coding and/or non-coding sequences.

The present invention further relates to variants of the herein above described polynucleotides which encode for fragments, analogs and derivatives of the polypeptide having the deduced amino acid sequence of FIG. 1 (SEQ ID NO:2). A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

The present invention includes polynucleotides encoding the same mature polypeptide as shown in FIG. 1 (SEQ ID NO:2). Further, the invention includes variants of such polynucleotides that encode a fragment, derivative or analog of the polypeptide of FIG. 1 (SEQ ID NO:2). Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Variants of the invention may have a sequence that occurs in nature or they may have a sequence that does not occur naturally. As herein above indicated, the polynucleotide may have a coding sequence which is a naturally occurring allelic variant of the coding sequence shown in FIG. 1 (SEQ ID NO:1). As known in the art, an allelic variant is an alternate form of a polynucleotide sequence which may have a substitution, deletion or addition of one or more nucleotides.

Among the particularly preferred embodiments of the invention in this regard are polynucleotides encoding polypeptides having the amino acid sequence of Cytostatin III set out in FIG. 1 (SEQ ID NO:2); variants, analogs, derivatives and fragments thereof, and fragments of the variants, analogs and derivatives Further particularly preferred in this regard are polynucleotides encoding Cytostatin III variants, analogs, derivatives and fragments, and variants, analogs and derivatives of the fragments, which have the amino acid sequence of the Cytostatin III polypeptide of FIG. 1 (SEQ ID NO:2) in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the Cytostatin III. Also especially preferred in this regard are conservative substitutions. Most highly preferred are polynucleotides encoding polypeptides having the amino acid sequence of FIG. 1 (SEQ ID NO:2), without substitutions.

Also particularly preferred in this regard are polynucleotides encoding a polypeptide having the amino acid sequence of the Cytostatin III set out in FIG. 1 (SEQ ID NO:2). As set out elsewhere herein, the polynucleotide may encode the polypeptide in a continuous region or in a plurality of two or more discontinuous exons, and it may comprise additional regions as well, which are unrelated to the coding region or regions.

Most highly preferred in this regard are polynucleotides that comprise a region that is more than 85% identical to the Cytostatin III-encoding portion of the polynucleotide set out in FIG. 1 (SEQ ID NO:1). Alternatively, most highly preferred are polynucleotides that comprise a region that is more than 85% identical to the Cytostatin III-encoding portion of the cDNA the deposited clone. Among such polynucleotides, those more than 90% identical to the same are particularly preferred, and, among these particularly preferred polynucleotides, those with 95% or more identity are especially preferred. Furthermore, those with 97% or more identity are highly preferred among those with 95% or more identity, and among these those with 98% or more and 99% or more identity are particularly highly preferred, with 99% or more being the more preferred of these.

The present invention also includes polynucleotides in which the sequence encoding the mature polypeptide is fused in the same reading frame to additional sequences. Such sequences include signal sequences, which facilitate transport of the nascent protein into the endoplasmic reticulum, pro-sequences that are associated with inactive precursor forms of the polypeptide, which may facilitate trafficking of the protein in a cell or out of a cell or may improve persistence of the protein in a cell or in an extracellular compartment. Such sequences also may be added to facilitate production and purification, or to add additional functional domains, as discussed elsewhere herein.

Thus, polynucleotides of the invention may encode, in addition to a mature cytostatin, particularly Cytostatin III, for example, a leader sequence, such as a signal peptide which functions as a secretory sequence for controlling transport of the polypeptide into the lumen of the endoplasmic reticulum. The leader sequence may be removed by the host cell, as is generally the case for signal peptides, yielding another precursor protein or the mature polypeptide. A precursor protein having a leader sequence often is called a preprotein.

A polynucleotide of the present invention may encode a mature or precursor pre-, pro- or prepropolypeptide as discussed above, among others, fused to additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the vector pQE-9, among others, many of which are commercially available. As described in Gentz et al., Proc. Natl. Acad. Sci., USA 86: 821–824 (1989), for instance, hexa-histidine provides for convenient purification of the fusion protein. Typically, it does not adversely affect protein structure or function, and it binds efficiently, selectively and tightly to metal chelate resins, particularly nickel chelate resins. For instance, as is well known, hexa-histidine tags often bind especially well to nickel-NTA resin, which is well known and readily available and can be obtained commercially from, for instance, Qiagen. Moreover, the histidine-metal interaction not only is stable to a variety of conditions useful to remove non-specifically bound material, but also the fusion polypeptide can be bound and removed under mild, non-denaturing conditions. The hexa-histidine tag can be fused most conveniently to the amino or the carboxyl terminus of the cytostatin polypeptide. A tag of the hexa-histidine type is particularly useful for bacterial expression.

Another useful marker sequence in certain other preferred embodiments is a hemagglutinin ("HA") tag, particularly when a mammalian cell is used for expression; e.g., COS-7 cells. The HA tag corresponds to an epitope derived of influenza hemagglutinin protein, which has been described by Wilson et al., Cell 37: 767 (1984), for instance. The present invention further relates to polynucleotides that hybridize to the herein above-described cytostatin sequences, particularly Cytostatin III sequences. Preferred in this regard are polynucleotides that have at least 50% identity to the sequences described herein above. Particularly preferred are sequences that have at least 70% identity. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, a probe as discussed above, derived from the full length Cytostatin III cDNA, including the entire Cytostatin III cDNA of FIG. 1 (SEQ ID NO:1) or of the deposited clone, or the coding region of thereof, or any part thereof useful as a probe, may be used as a hybridization probe for cDNA and genomic DNA to isolate full-length cDNAs and genomic clones encoding Cytostatin III and to isolate cDNA and genomic clones of other genes that have a high sequence similarity to the human Cytostatin III gene. Such probes generally will comprise at least 20 bases. Preferably, such probes will have at least 30 bases. Particularly preferred probes will have at least 30 bases and will have 50 bases or less.

For example, the coding region of the Cytostatin III gene may be isolated by screening using the known DNA sequence to synthesize an oligonucleotide probe. Labeled an oligonucleotide having a sequence complementary to that of a gene of the present invention then is used to screen a library of human cDNA, genomic DNA or mRNA to determine which members of the library the probe hybridizes to.

The polynucleotides and polypeptides of the present invention may be employed as research reagents and materials for discovery of treatments and diagnostics to human disease, as further discussed herein relating to polynucleotide assays, inter alia.

The polynucleotides also may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited Materials

The cDNA deposit is referred to herein as "the deposited clone" or as "the cDNA of the deposited clone." The deposited clone was deposited with the American Type Culture Collection, 10301 University volevar manassas, virginia 2011-2209 USA, on Nov. 6, 1995 and assigned ATCC Deposit No. 97332.

The deposited material is a pBluescript SK (−) plasmid (Stratagene, La Jolla, Calif.) that contains the full length human Cytostatin III cDNA.

The deposit has been made under the terms of the Budapest Treaty on the International Recognition of the Deposit of Micro-organisms for purposes of Patent Procedure. The deposit is provided merely as convenience to those of skill in the art and it is not an indication or an admission that a deposit is required for enablement, such as that required under 35 U.S.C. §112.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. § 112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials, and no such license is hereby granted.

Polypeptides

The present invention further relates to a human Cytostatin III polypeptide which has the deduced amino acid sequence of FIG. 1 (SEQ ID NO:2) or which has the amino acid sequence encoded by the deposited clone.

The invention also relates to fragments, analogs and derivatives of these polypeptides. The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments it is a recombinant polypeptide.

The fragment, derivative or analog of the polypeptide of FIG. 1 (SEQ ID NO:2) or that encoded by the cDNA in the deposited clone may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of Cytostatin III set out in FIG. 1 (SEQ ID NO:2), variants, analogs, derivatives and fragments thereof, and variants, analogs and derivatives of the fragments. Alternatively, particularly preferred embodiments of the invention in this regard are polypeptides having the amino acid sequence of the Cytostatin III of the cDNA in the deposited clone, variants, analogs, derivatives and fragments thereof, and variants, analogs and derivatives of the fragments.

Further particularly preferred in this regard are variants, analogs, derivatives and fragments, and variants, analogs and derivatives of the fragments, having the amino acid sequence of the Cytostatin III polypeptide of FIG. 1 (SEQ ID NO:2) or of the eDNA in the deposited clone, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the Cytostatin III. Also especially preferred in this regard are conservative substitutions. Most highly preferred are polypeptides having the amino acid sequence of FIG. 1 (SEQ ID NO:2) or the deposited clone without substitutions.

The polypeptides and polynucleotides of the present invention are preferably provided in an isolated form, and preferably are purified to homogeneity.

The term "isolated" means that the material has been altered from its natural state; e.g., that, if it occurs in nature, it has been removed from its original environment. For example, a naturally Occurring polynucleotide or polypeptide naturally present in a living animal in its natural state is not "isolated," but the same polynucleotide or polypeptide separated from some or all of the coexisting materials in the natural system is "isolated", as the term is employed herein.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media formulation, a solution for introduction into cells, a composition or solution for chemical or enzymatic reaction, and the like, which are not naturally compositions, and therein remain isolated polynucleotides or polypeptides within the meaning of that term as it is employed herein.

Fragments

Also among preferred embodiments of this aspect of the present invention are polypeptides comprising fragments of Cytostatin III, most particularly fragments of the Cytostatin III having the amino acid set out in FIG. 1 (SEQ ID NO:2), or having the amino acid sequence of the Cytostatin III of the deposited clone, and fragments of variants and derivatives of the Cytostatin III of FIG. 1 (SEQ ID NO:2) or of the deposited clone.

In this regard a fragment is a polypeptide having an amino acid sequence that entirely is the same as part but not all of the amino acid sequence of the aforementioned Cytostatin III polypeptides and variants or derivatives thereof.

Such fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a Cytostatin III polypeptide of the present comprised within a precursor polypeptide designed for expression in a host and having heterologous pre and pro-polypeptide regions fused to the amino terminus of the Cytostatin III fragment and an additional region fused to the carboxyl terminus of the fragment. Therefore, fragments in one aspect of the meaning intended herein, refers to the portion or portions of a fusion polypeptide or fusion protein derived from Cytostatin III.

Among preferred fragments of Cytostatin III are fragments about 5–15, 10–20, 15–40, 25–50, 35–60, 50–75, 65–80, 65–90, 65–100, 50–100, 75–100, 90–115, 80–135, 90–130, 100–125 and 110–135 amino acids long.

In this context about includes the particularly recited range and ranges larger or smaller by several, a few, 5, 4, 3, 2 or 1 amino acid at either extreme or at both extremes. For instance, about 65–90 amino acids in this context means a polypeptide fragment of 65, 65 plus or minus several, a few, 5, 4, 3, 2 or 1 amino acid to 90 or 90 plus or minus several a few, 5, 4, 3, 2 or 1 amino acid residues, i.e., ranges a broad as 65 minus several amino acids to 90 plus several amino acids to as narrow as 65 plus several amino acids to 90 minus several amino acids.

Highly, preferred in this regard are the recited ranges plus or minus as many as 5 amino acids at either or at both extremes. Particularly highly preferred are the recited ranges means plus or minus as many as 3 amino acids at either or at both extremes. Especially particularly highly preferred are ranges plus or minus 1 amino acid at either or at both extremes. Most highly preferred of all in this regard are fragments 5–15, 10–20, 15–40, 25–50, 35–60, 50–75, 65–80, 65–90, 65–100, 50–100, 75–100, 90–115, 80–135, 90–130, 100–125 and 110–135 amino acids in length are preferred.

Among especially preferred fragments of the invention are truncation mutants of Cytostatin III. Truncation mutants include Cytostatin III polypeptides having the amino acid sequence of FIG. 1 (SEQ ID NO:2), or of the deposited clone, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Fragments having the size ranges set out about also are preferred embodiments of truncation fragments, which are especially preferred among fragments generally.

Also preferred in this aspect of the invention are fragments characterized by structural or functional attributes of Cytostatin III. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of Cytostatin III.

Certain preferred regions in these regards are set out in FIG. 3, and include, but are not limited to, regions of the aforementioned types identified by analysis of the amino acid sequence set out in FIG. 1 (SEQ ID NO:2). As set out in FIG. 3, such preferred regions include Garnier-Robson alpha-regions, beta-regions, turn-regions and coil-regions, Chou-Fasman alpha-regions, beta-regions and turn-regions, Kyte-Doolittle hydrophilic regions and hydrophilic regions, Eisenberg alpha and beta amphipathic regions, Karplus-Schulz flexible regions, Emini surface-forming regions and Jameson-Wolf high antigenic index regions.

Among highly preferred fragments in this regard are those that comprise regions of Cytostatin III that combine several structural features, such as several of the features set out above. In this regard, the regions defined by the residues about 10 to about 20, about 40 to about 50, about 70 to about 90 and about 100 to about 110 of FIG. 1 (SEQ ID NO:2), which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of Cytostatin III. Most highly preferred in this regard are fragments that have a chemical, biological or other activity of Cytostatin III, including those with a similar activity or an improved activity, or with a decreased undesirable activity. Highly preferred in this regard are fragments that contain regions that are homologs in sequence, or in position, or in both sequence and to active regions of related polypeptides, such as the related polypeptides set out in FIG. 2 (SEQ ID NO:11–15), which include Mouse MDGI, Bovine MDGI, Human MDGI, Cytostatin I and Cytostatin II. Among particularly preferred fragments in these regards are truncation mutants, as discussed above.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspondent to the preferred fragments, as discussed above.

Vectors, Host Cells, Expression

The present invention also relates to vectors which include polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate, polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation also may be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. cited above, which is illustrative of the many laboratory manuals that detail these techniques.

In accordance with this aspect of the invention the vector may be, for example, a plasmid vector, a single or double-stranded phage vector, a single or double-stranded RNA or DNA viral vector. Such vectors may be introduced into cells as polynucleotides, preferably RNA, by well known techniques for introducing DNA and RNA into cells. The vectors, in the case of phage and viral vectors also may be and preferably are introduced into cells as packaged or encapsidated virus by well known techniques for infection and transduction. Viral vectors may be replication competent or replication defective. In the latter case viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate transacting factors either are supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, from bacteriophage, from yeast episomes, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids, all may be used for expression in accordance with this aspect of the present invention. Generally, any vector suitable to maintain, propagate or express polynucleotides to express a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skill, are set forth in great detail in Sambrook et al. cited elsewhere herein.

The DNA sequence in the expression vector is operatively linked to appropriate expression control sequence(s), including, for instance, a promoter to direct mRNA transcription. Representatives of such promoters include the phage lambda PL promoter, the E. coli lac, trp and tac promoters, the SV40 early and late promoters and promoters of retroviral LTRs, to name just a few of the well-known promoters. It will be understood that numerous promoters not mentioned are suitable for use in this aspect of the invention are well known and readily may be employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription, such as repressor binding sites and enhancers, among others.

Vectors for propagation and expression generally will include selectable markers. Such markers also may be suitable for amplification or the vectors may contain additional markers for this purpose. In this regard, the expression vectors preferably contain one or more selectable marker genes to provide a phenotypic trait for selection of transformed host cells. Preferred markers include dihydrofolate reductase or neomycin resistance for eukaryotic cell culture, and tetracycline or ampicillin resistance genes for culturing E. coli and other bacteria.

The vector containing the appropriate DNA sequence as described elsewhere herein, as well as an appropriate promoter, and other appropriate control sequences, may be introduced into an appropriate host using a variety of well known techniques suitable to expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts for of a great variety of expression constructs are well known, and those of skill will be enabled by the present disclosure readily to select a host for expressing a polypeptides in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ and promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Selection of appropriate vectors and promoters for expression in a host cell is a well known procedure and the requisite techniques for expression vector construction, introduction of the vector into the host and expression in the host are routine skills in the art.

The present invention also relates to host cells containing the above-described constructs discussed above. The host cell can be a higher eukaryotic cell, such as a mammalian cell, or a lower eukaryotic cell, such as a yeast cell, or the host cell can be a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al. BASIC METHODS IN MOLECULAR BIOLOGY, (1986).

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., MOLECULAR CLONING: A LABORATORY MANUAL, 2nd Ed., Cold Spring Harbor Laboratory Press, Cold Spring Harbor, N.Y. (1989).

Generally, recombinant expression vectors will include origins of replication, a promoter derived from a highly-expressed gene to direct transcription of a downstream structural sequence, and a selectable marker to permit isolation of vector containing cells after exposure to the vector.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Polynucleotides of the invention, encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiating AUG. Also, generally, there will be a translation stop codon at the end of the polypeptide and there will be a polyadenylation signal and a transcription termination signal appropriately disposed at the 3' end of the transcribed region.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, region also may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, where the selected promoter is inducible it is induced by appropriate means (e.g., temperature shift or exposure to chemical inducer) and cells are cultured for an additional period.

Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can be employed for expression, as well. Examples of mammalian expression systems include the COS-7 lines of monkey kidney fibroblast, described in Gluzman et al., Cell 23: 175 (1981). Other cell lines capable of expressmg a compatible vector include for example, the C127, 3T3, CHO, HeLa, human kidney 293 and BHK cell lines.

The Cytostatin III polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HBPLC") is employed for purification. Well known techniques for refolding protein may be employed to regenerate active conformation when the polypeptide is denatured during isolation and or purification.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Cytostatin III polynucleotides and polypeptides may be used in accordance with the present invention for a variety of applications, particularly those that make use of the chemical and biological properties Cytostatin III. Among these are applications in characterizing cells and organisms and in growing cells and organisms. Additional applications relate to diagnosis and to treatment of disorders of cells, tissues and organisms. These aspects of the invention are illustrated further by the following discussion.

Polynucleotide Assays This invention is also related to the use of the Cytostatin III polynucleotides to detect complementary polynucleotides such as, for example, as a diagnostic reagent. Detection of a mutated form of Cytostatin III associated with a dysfunction will provide a diagnostic tool that can add or defme a diagnosis of a disease or susceptibility to a disease which results from under-expression over-expression or altered expression of Cytostatin III, such as, for example, breast cancer.

Individuals carrying mutations in the human Cytostatin III gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324: 163–166 (1986)). RNA or cDNA may also be used in the same ways. As an example, PCR primers complementary to the nucleic acid encoding Cytostatin III can be used to identify and analyze Cytostatin III expression and mutations. For example, deletions and insertions can be detected by a change in size of the amplified product in comparison to the normal genotype. Point mutations can be identified by hybridizing amplified DNA to radiolabeled Cytostatin III RNA or alternatively, radiolabeled Cytostatin III antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230: 1242 (1985)). Sequence changes at specific locations also may be revealed by nuclease protection assays, such as RNase and S1 protection or the chemical cleavage method (e.g., Cotton et al., Proc. Natl. Acad. Sci., USA, 85: 4397–4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Chromosome Assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a Cytostatin III gene. This can be accomplished using a variety of well known techniques and libraries, which generally are available commercially. The genomic DNA the is used for in situ chromosome mapping using well known techniques for this purpose. Typically, in accordance with routine procedures for chromosome mapping, some trial and error may be necessary to identify a genomic probe that gives a good in situ hybridization signal.

In some cases, in addition, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of the clones from which the express sequence tag (EST) was derived, and the longer the better. For example, 2,000 bp is good, 4,000 is better, and more than 4,000 is probably not necessary to get good results a reasonable percentage of the time. For a review of this technique, see Verma et al., HUMAN CHROMOSOMES: A MANUAL OF BASIC TECHNIQUES, Pergamon Press, New York (1988).

Once a sequence has been mapped to a precise chromosomal location, the physical position of the sequence on the chromosome can be correlated with genetic map data. Such data are found, for example, in V. McKusick, MENDELIAN INHERITANCE IN MAN, available on line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Polypeptide Assays

The present invention also relates to a diagnostic assays such as quantitative and diagnostic assays for detecting levels of Cytostatin III protein in cells and tissues, including determination of normal and abnormal levels. Thus, for instance, a diagnostic assay in accordance with the invention for detecting over-expression of Cytostatin III protein compared to normal control tissue samples may be used to detect the presence of myocardial infarction, for example. Assay techniques that can be used to determine levels of a protein, such as an Cytostatin III protein of the present invention, in a sample derived from a host are well-known to those of skill in the art. Such assay methods include radioimmunoassays, competitive-binding assays, Western Blot analysis and ELISA assays. Among these ELISAs frequently are preferred. An ELISA assay initially comprises preparing an antibody specific to Cytostatin III, preferably a monoclonal antibody. In addition a reporter antibody generally is prepared which binds to the monoclonal antibody. The reporter antibody is attached a detectable reagent such as radioactive, fluorescent or enzymatic reagent, in this example horseradish peroxidase enzyme.

To carry out an ELISA a sample is removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any Cytostatin III proteins attached to the polystyrene dish. Unbound monoclonal antibody is washed out with buffer. The reporter antibody linked to horseradish peroxidase is placed in the dish resulting in binding of the reporter antibody to any monoclonal antibody bound to Cytostatin III. Unattached reporter antibody is then washed out. Reagents for peroxidase activity, including a colorimetric substrate are then added to the dish. Immobilized peroxidase, linked to Cytostatin III through the primary and secondary antibodies, produces a colored reaction product. The amount of color developed in a given time period indicates the amount of Cytostatin III protein present in the sample. Quantitative results typically are obtained by reference to a standard curve.

A competition assay may be employed wherein antibodies specific to Cytostatin III attached to a solid support and labeled Cytostatin III and a sample derived from the host are passed over the solid support and the amount of label detected attached to the solid support can be correlated to a quantity of Cytostatin III in the sample.

Immunoassays and Reagents

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., Nature 256: 495–497 (1975), the trioma technique, the human B-cell hybridoma technique (Kozbor et al., Immunology Today 4: 72 (1983) and the EBV-hybridoma technique to produce human monoclonal antibodies (Cole et al., pg. 77–96 in MONOCLONAL ANTIBODIES AND CANCER THERAPY, Alan R. Liss, Inc. (1985).

Techniques described for the production of single chain antibodies (U.S. Pat. No. 4,946,778) can be adapted to produce single chain antibodies to immunogenic polypeptide products of this invention. Also, transgenic mice, or other organisms such as other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Thus, among others, the growth inhibitory and differentiation stimulating activity of Cytostatin III is useful to inhibit growth and stimulate differentiation of tumor cells, for instance in vitro, as for growth of cells for research, industrial or commercial purposes, for example. The same activities may be applied to treatment of aberrant cell growth in an organism, such as growth of cells of a tumor. In these regards, Cytostatin III polypeptides are preferred, particularly the Cytostatin III having the amino acid sequence set out in FIG. 1 (SEQ ID NO:2) or the amino acid sequence of the Cytostatin III of the cDNA of the deposited clone.

Similarly, the ability of Cytostatin III to inhibit growth of Cytostatin III-sensitive cells, such as Cytostatin III-sensitive endothelial cells, including, for instance, venus endothelial cells, may be used to prevent, slow or alter cell growth in culture or in situ. Often, tumor cells, such as those at an original tumor and those at sites of metastasis, must attract new blood vessels to grow. Cytostatin III may be used to inhibit Cytostatin III-sensitive cells involved in tumor vascularization, such as Cytostatin III-sensitive venus endothelial cells for instance, and may be useful slow tumor growth, or reduce metastatic potential of tumors or slow progression of metastatic disease.

Cytostatin III also may be useful to modulate b-adrenergic activity of certain Cytostatin III-sensitive cells, such as Cytostatin III-sensitive cardiac myocytes.

Furthermore, activity of Cytostatin III, such as activity that modulates mammary gland differentiation or affects the growth of mammary epithelial cells may be used to promote formation of alveolar buds, aid development of differentiated lobuloalveoli, and stimulate the production of milk protein and the accumulation of fat droplets. Such lactation-stimulating activity may aid milk production in commercial milk-producing mammals. It also may be useful to aid milk-production by human mothers, for instance. In a related application, modulating activity of Cytostatin III that affects breast size may be useful to aid return of an enlarged breast to normal size after parturition. Inhibition of Cytostatin III activity, for instance, by antisense phosphorothioates or by antibodies, may be useful for selective inhibition of endogenous Cytostatin III activity in mammary epithelial cells to suppress the appearance of alveolar end buds and to lower the beta-casein level.

As set out further below, these and other activities and properties of the Cytostatin III polynucleotides and polypeptides of the invention have various applications and uses in numerous fields including applications involving growth of cells in vitro, commercial production of milk and milk products, and diagnosis and treatments relating to the fields of oncology, cardiology, immunology, endocrinology, hematology, metabolic disorders, musculoskelatal problems and gynecology and obstetrics, to name a few.

Cytostatin III Binding Molecules and Assays

This invention also provides a method for identification of molecules, such as receptor molecules, that bind Cytostatin III. Genes encoding proteins that bind Cytostatin III, such as receptor proteins, can be identified by numerous methods known to those of skill in the art, for example, ligand panning and FACS sorting. Such methods are described in many laboratory manuals such as, for instance, Coligan et al., Current Protocols in Immunology 1(2): Chapter 5 (1991).

For instance, expression cloning may be employed for this purpose. To this end polyadenylated RNA is prepared from a cell responsive to Cytostatin III, a cDNA library is created from this RNA, the library is divided into pools and the pools are transfected individually into cells that are not responsive to Cytostatin III. The transfected cells then are exposed to labeled Cytostatin III. (Cytostatin III can be labeled by a variety of well-known techniques including standard methods of radio-iodination or inclusion of a recognition site for a site-specific protein kinase.) Following exposure, the cells are fixed and binding of cytostatin is determined. These procedures conveniently are carried out on glass slides.

Pools are identified of cDNA that produced Cytostatin III-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively a labeled ligand can be photoaffinity linked to a cell extract, such as a membrane or a membrane extract, prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess Cytostatin III binding capacity of Cytostatin III binding molecules, such as receptor molecules, in cells or in cell-free preparations.

Agonists and Antagonists—assays and Molecules

The invention also provides a method of screening compounds to identify those which enhance or block the action of Cytostatin III on cells, such as its interaction with Cytostatin 111-binding molecules such as receptor molecules. An agonist is a compound which increases the natural biological functions of Cytostatin III or which functions in a manner similar to Cytostatin III, while antagonists decrease or eliminate such functions.

For example, a cellular compartment, such as a membrane or a preparation thereof, such as a membrane-preparation, may be prepared from a cell that expresses a molecule that binds Cytostatin III, such as a molecule of a signaling or regulatory pathway modulated by Cytostatin III. The preparation is incubated with labeled Cytostatin III in the absence or the presence of a candidate molecule which may be a Cytostatin III agonist or antagonist. The ability of the candidate molecule to bind the binding molecule is reflected in decreased binding of the labeled ligand. Molecules which bind gratuitously, i.e., without inducing the effects of Cytostatin III on binding the Cytostatin III binding molecule, are most likely to be good antagonists. Molecules that bind well and elicit effects that are the same as or closely Cytostatin III-like effects of potential agonists and antagonists may by measured, for instance, by determining activity of a second messenger system following interaction of the candidate molecule with a cell or appropriate cell preparation, and comparing the effect with that of Cytostatin III or molecules that elicit the same effects as Cytostatin III. Second messenger systems that may be useful in this regard include but are not limited to AMP guanylate cyclase, ion channel or phosphoinositide hydrolysis second messenger systems.

Another example of an assay for Cytostatin III antagonists is a competitive assay that combines Cytostatin III and a potential antagonist with membrane-bound Cytostatin III receptor molecules or recombinant Cytostatin III receptor molecules under appropriate conditions for a competitive inhibition assay. Cytostatin III can be labeled, such as by radioactivity, such that the number of Cytostatin III molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing Cytostatin III-induced activities, thereby preventing the action of Cytostatin III by excluding Cytostatin III from binding.

Potential antagonists include a small molecule which binds to and occupies the binding site of the polypeptide thereby preventing binding to cellular binding molecules, such as receptor molecules, such that normal biological activity is prevented. Examples of small molecules include but are not limited to small organic molecules, peptides or peptide-like molecules.

Other potential antagonists include antisense molecules. Antisense technology can be used to control gene expression through antisense DNA or RNA or through triple-helix formation. Antisense techniques are discussed, for example, in—Okano, J. Neurochem. 56: 560 (1991); OLIGODEOXY-NUCLEOTIDES AS ANTISENSE INHIBITORS OF GENE EXPRESSION, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251:

1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Cytostatin III. The antisense RNA oligonucleotide hybridizes to the mRNA in vivo and blocks translation of the MRNA molecule into Cytostatin III polypeptide. The oligonucleotides described above can also be delivered to cells such that the antisense RNA or DNA may be expressed in vivo to inhibit production of Cytostatin III.

The antagonists may be employed in a composition with a pharmaceutically acceptable carrier, e.g., as hereinafter described.

The antagonists may be employed for instance to treat cardiac myocte hypertrophy or leukemia Compositions The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 mg/kg body weight. In most cases they will be administered in an amount not in excess of about 8 mg/kg body weight per day. Preferably, in most cases, dose is from about 10 mg/kg to about 1 mg/kg body weight, daily. It will be appreciated that optimum dosage will be determined by standard methods for each treatment modality and indication, taking into account the indication, its severity, route of administration, complicating conditions and the like.

Gene Therapy

The Cytostatin III polynucleotides, polypeptides, agonists and antagonists that are polypeptides may be employed in accordance with the present invention by expression of such polypeptides in vivo, in treatment modalities often referred to as "gene therapy."

Thus, for example, cells from a patient may be engineered with a polynucleotide, such as a DNA or RNA, encoding a polypeptide ex vivo, and the engineered cells then can be provided to a patient to be treated with the polypeptide. For example, cells may be engineered ex vivo by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct then may be isolated and introduced into a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

Such vectors well include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques 7: 980–990 (1989), or any other promoter (e.g., cellular promoters such as eukaryotic cellular promoters including, but not limited to, the histone, RNA polymerase III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the B-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., Human Gene Therapy 1: 5–14 (1990). The vector may be transduced into the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplification's, while illustrating certain specific aspects of the invention, do not portray the limitations or circumscribe the scope of the disclosed invention.

Certain terms used herein are explained in the foregoing glossary.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989), herein referred to as "Sambrook."

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook and numerous other references such as, for instance, by Goeddel et al., Nucleic Acids Res. 8: 4057 (1980).

Unless described otherwise, ligations were accomplished using standard buffers, incubation temperatures and times, approximately equimolar amounts of the DNA fragments to be ligated and approximately 10 units of T4 DNA ligase ("ligase") per 0.5 mg of DNA.

Example 1
Expression and Purification of Human Cytostatin III Using Bacteria The DNA sequence encoding human Cytostatin III in the deposited polynucleotide was amplified using PCR oligonucleotide primers specific to the amino acid carboxyl terminal sequence of the human Cytostatin III protein and to vector sequences 3' to the gene. Additional nucleotides containing restriction sites to facilitate cloning were added to the 5' and 3' sequences respectively.

The 5' oligonucleotide primer had the sequence 5' CGC GCA TGC CTC CCA ACC TCA C 3' (SEQ ID NO:3) containing the underlined SphI restriction site, which encodes a start AUG, followed by 13 nucleotides of the human Cytostatin III coding sequence set out in FIG. 1 (SEQ ID NO:1) beginning with the second base of the second codon.

The 3' primer had the sequence 5' GCG AAG CTT CTA TCT GAC CTT CCT G 3' (SEQ ID NO:4) containing the underlined Hind III restriction site followed by 16 nucleotides complementary to the last 16 nucleotides of the Cytostatin III coding sequence set out in FIG. 1 (SEQ ID NO:1), including the stop codon.

The restrictions sites were convenient to restriction enzyme sites in the bacterial expression vectors pQE-7, which were used for bacterial expression in these examples. (Qiagen, Inc. 9259 Eton Avenue, Chatsworth, Calif., 91311). pQE-7 encodes ampicillin antibiotic resistance ("Ampr") and contains a bacterial origin of replication ("ori"), an IPTG inducible promoter, a ribosome binding site ("RBS"), a 6-His tag and restriction enzyme sites.

The amplified human Cytostatin III DNA and the vector pQE-7 both were digested with SphI and HindIII, and the digested DNAs then were ligated together. Insertion of the Cytostatin III DNA into the Sph1/HindIII restricted vector placed the Cytostatin III coding region downstream of and operably linked to the vector's IPTG-inducible promoter and in-frame with an initiating AUG appropriately positioned for translation of Cytostatin III.

The ligation mixture was transformed into competent E. coli cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kanr"), was used in carrying out the illustrative example described here. This strain, which is only one of many that are suitable for expressing Cytostatin III, is available commercially from Qiagen.

Transformants were identified by their ability to grow on LB plates in the presence of ampicillin. Plasmid DNA was isolated from resistant colonies and the identity of the cloned DNA was confirmed by restriction analysis.

Clones containing the desired constructs were grown overnight ("O/N") in liquid culture in LB media supplemented with both ampicillin (100 ug/ml) and kanamycin (25 ug/nil).

The O/N culture was used to inoculate a large culture, at a dilution of approximately 1:100 to 1:250. The cells were grown to an optical density at 600 nm ("OD600") of between 0.4 and 0.6. Isopropyl-B-D-thiogalactopyranoside ("IPTG") was then added to a final concentration of 1 mM to induce transcription from lac repressor sensitive promoters, by inactivating the lacI repressor. Cells subsequently were incubated further for 3 to 4 hours. Cells then were harvested by centrifugation and disrupted, by standard methods. Inclusion bodies were purified from the disrupted cells using routine collection techniques, and protein was solubilized from the inclusion bodies into 8M urea. The 8M urea solution containing the solubilized protein was passed over a PD-10 column in 2x phosphate buffered saline ("PBS"), thereby removing the urea, exchanging the buffer and refolding the protein. The protein was purified by a firther step of chromatography to remove endotoxin. Then, it was sterile filtered. The sterile filtered protein preparation was stored in 2xPBS at a concentration of 95 micrograms per mL.

Analysis of the preparation by standard methods of polyacrylamide gel electrophoresis revealed that the preparation contained about 80% monomer Cytostatin III having the expected molecular weight of, approximately, 14 kDa.

Example 2

Cloning and Expression of Human Cytostatin III in a Baculovirus Expression System The cDNA sequence encoding the full length human Cytostatin III protein, in the deposited clone is amplified using PCR oligonucleotide primers corresponding to the 5' and 3' sequences of the gene:

The 5' primer has the sequence 5' GC GGA TCC TCC CAA CCT CAC TGG CTA C 3' (SEQ ID NO:5) containing the underlined BamH1 restriction enzyme site followed by 19 bases of the sequence of Cytostatin III of FIG. 1 (SEQ ID NO:1). Inserted into an expression vector, as described below, the 5' end of the amplified fragment encoding human Cytostatin III provides an efficient signal peptide. An efficient signal for initiation of translation in eukaryotic cells, as described by Kozak, M., J. Mol. Biol. 196: 947–950 (1987) is appropriately located in the vector portion of the construct The 3' primer has the sequence 5' GC GGT ACC CTA TCT GAC CTT CCT G 3' (SEQ ID NO:6) containing the Asp718 restriction followed by nucleotides complementary to the last 16 nucleotides of the Cytostatin III coding sequence set out in FIG. 1 (SEQ ID NO:1), including the stop codon.

The amplified fragment is isolated from a 1% agarose gel using a commercially available kit ("Geneclean," BIO 101. Inc., La Jolla, Calif.). The fragment then is digested with BamH1 and Asp718 and again is purified on a 1% agarose gel. This fragment is designated herein F2.

The vector pA2-GP is used to express the Cytostatin III protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the Autographa califomica nuclear polyhedrosis virus (AcMNPV) followed by convenient restriction sites. The signal peptide of AcMNPV gp67, including the N-terminal methionine, is located just upstream of a BamH1 site. The polyadenylation site of the simian virus 40 ("SV40") is used for efficient polyadenylation. For an easy selection of recombinant virus the beta-galactosidase gene from E.coli is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., Virology 170: 31–39, among others.

The plasmid is digested with the restriction enzymes BamH1 and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. E. coli HB101 cells are transformed with ligation mix and spread on culture plates.

Bacteria are identified that contain the plasmid with the human Cytostatin III gene by digesting DNA from individual colonies using BamH1 and Asp718 and then analyzing the digestion product by gel electrophoresis. The sequence of the cloned fragment is confirmed by DNA sequencing. This plasmid is designated herein pBacCytostatin III.

1 mg of the plasmid pBacCytostatin III is co-transfected with 1.0 mg of a commercially available linearized baculovirus DNA ("BaculoGoldÔ baculovirus DNA", Pharmingen, San Diego, Calif.), using the lipofection method described by Felgner et al., Proc. Natl. Acad. Sci. USA 84: 7413–7417 (1987). 1 mg of BaculoGoldÔ virus DNA and 5 mg of the plasmid pBacCytostatin III are mixed in a sterile well of a microtiter plate containing 50 ml of serum free Grace's medium (Life Technologies Inc., Gaithersburg, Md.). Afterwards 10 ml Lipofectin plus 90 ml Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 ml of Grace's medium. The agar is removed by a brief centrifugation and the supernatant containing the recombinant baculovirus is used to infect Sf9 cells seeded in 35 mm dishes. Four days later the supernatants, of these culture dishes are harvested and then they are stored at 4° C. A clone containing properly inserted Cytostatin III is identified by DNA analysis including restriction mapping and sequencing. This is designated herein as V-Cytostatin III.

Sf9 cells are grown in Grace's medium supplemented with 10% heat-inactivated FBS. The cells are infected with the recombinant baculovirus V-Cytostatin III at a multiplicity of infection ("MOI") of about 2 (about 1 to about 3). Six hours later the medium is removed and is replaced with SF900 II medium minus methionine and cysteine (available from Life Technologies Inc., Gaithersburg). 42 hours later, 5 mCi of 35S-methionine and 5 mCi 35S cysteine (available from Amersham) are added. The cells are further incubated for 16 hours and then they are harvested by centrifugation, lysed and the labeled proteins are visualized by SDS-PAGE and autoradiography. Active proteins are then produced by dialysis with PBS.

Example 3

Expression of Cytostatin III in COS Cells

The expression plasmid, Cytostatin III HA, is made by cloning a cDNA encoding Cytostatin III into the expression vector pcDNAI/Amp (which can be obtained from Invitrogen, Inc.).

The expression vector pcDNAI/amp contains: (1) an E. coli origin of replication effective for propagation in E. coli and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 ntron and the polyadenylation signal by means of restriction sites in the polylinker.

A DNA fragment encoding the entire Cytostatin III precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., Cell 37: 767 (1984). The fusion of the HA tag to the target protein allows easy detection of the recombinant protein with an antibody that recognizes the HA epitope.

The plasmid construction strategy is as follows.

The Cytostatin III cDNA of the deposit clone of the deposited clone is amplified using primers that contained convenient restriction sites, much as described above regarding the construction of expression vectors for expression of Cytostatin III in *E. coli* and *S. fugiperda.*

To facilitate detection, purification and characterization of the expressed Cytostatin III, one of the primers contains a hemagglutinin tag ("HA tag") as described above.

Suitable primers include that following, which are used in this example.

The 5' primer, containing the underlined BamHI site, an AUG start codon and 5 codons thereafter, forming the hexapeptide haemaglutinin tag, has the following sequence: 5' GC GGA TCC ACC ATG CCT CCC AAC CTC ACT 3' (SEQ ID NO:7).

The 3' primer, containing the underlined XbaI site and 15 bp of 3' coding sequence (at the 3' end) has the following sequence: 5' GC TCT AGA TCA AGC GTA GTC TGG GAC GTC GTA TGG GTA TCT GAC CTT CCT GAA 3' (SEQ ID NO:8).

The PCR amplified DNA fragment and the vector, pcDNAI/Amp, are digested with and then ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates which then are incubated to allow growth of ampicillin resistant colonies. Plasmid DNA is isolated from resistant colonies and examined by restriction analysis and gel sizing for the presence of the Cytostatin III-encoding fragment.

For expression of recombinant Cytostatin III, COS cells are transfected with an expression vector, as described above, using DEAE-DEXTRAN, as described, for instance, in Sambrook et al., MOLECULAR CLONING: A LABORATORY MANUAL, Cold Spring Laboratory Press, Cold Spring Harbor, N.Y. (1989).

Cells are incubated under conditions for expression of Cytostatin III by the vector.

Expression of the Cytostatin III HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing 35S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 4

Tissue distribution of Cytostatin III Expression

Northern blot analysis is carried out to examine the levels of expression of Cytostatin III in human tissues, using methods described by, among others, Sambrook et al, cited above. Total cellular RNA samples are isolated with RNAzolÔ B system (Biotecx Laboratories, Inc. 6023 South Loop East, Houston, Tex. 77033).

About 10 mg of Total RNA is isolated from tissue samples. The RNA is size resolved by electrophoresis through a 1% agarose gel under strongly denaturing conditions. RNA is blotted from the gel onto a nylon filter, and the filter then is prepared for hybridization to a detectably labeled polynucleotide probe.

As a probe to detect mRNA that encodes Cytostatin III, the antisense strand of the coding region of the cDNA insert in the deposited clone is labeled to a high specific activity. The CDNA is labeled by primer extension, using the Prime-It kit, available from Stratagene. The reaction is carried out using 50 ng of the cDNA, following the standard reaction protocol as recommended by the supplier. The labeled polynucleotide is purified away from other labeled reaction components by column chromatography using a Select-G-50 column, obtained from 5-Prime–3-Prime, Inc. of 5603 Arapahoe Road, Boulder, Colo. 80303.

The labeled probe is hybridized to the filter, at a concentration of 1,000,000 cpm/ml, in a small volume of 7% SDS, 0.5 M NaPO4, pH 7.4 at 65° C., overnight. Thereafter the probe solution is drained and the filter is washed twice at room temperature and twice at 60° C. with 0.5×SSC, 0.1% SDS. The filter then is dried and exposed to film at −70° C. overnight with an intensifying screen. Autoradiography shows that mRNA for Cytostatin III is abundant in breast lymph node cells.

Example 5

Gene Therapeutic Expression of Human Cytostatin III

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted—the chunks of tissue remain fixed to the bottom of the flask—and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

Cytostatin cDNA capable of expressing active Cytostatin III, is isolated. The ends of the fragment are modified, if necessary, for cloning into the vector. For instance, 5" overhanging may be treated with DNA polymerase to create blunt ends. 3' overhanging ends may be removed using S1 nuclease. Linkers may be ligated to blunt ends with T4 DNA ligase.

Equal quantities of the Moloney murine leukemia virus linear backbone and the Cytostatin III fragment are mixed together and joined using T4 DNA ligase. The ligation mixture is used to transform E. Coli and the bacteria are then plated onto agar-containing kanamycin. Kanamycin phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the Cytostatin III gene is introduced into the packaging cells by standard techniques. Infectious viral particles containing the Cytostatin III gene are collected from the packaging cells, which now are called producer cells.

Fresh media is added to the producer cells, and after an appropriate incubation period media is harvested from the plates of confluent producer cells. The media, containing the infectious viral particles, is filtered through a Millipore filter to remove detached producer cells. The filtered media then is used to infect fibroblast cells. Media is removed from a sub-confluent plate of fibroblasts and quickly replaced with the filtered media. Polybrene (Aldrich) may be included in the media to facilitate transduction. After appropriate incubation, the media is removed and replaced with fresh media. If the titer of virus is high, then virtually all fibroblasts will be infected and no selection is required. If the titer is low, then it is necessary to, use a retroviral vector that has a selectable marker, such as neo or his, to select out transduced cells for expansion.

Engineered fibroblasts then may be injected into rats, either alone or after having been grown to confluence on microcarrier beads, such as cytodex 3 beads. The injected fibroblasts produce Cytostatin III product, and the biological actions of the protein are conveyed to the host.

It will be clear that the invention may be practiced otherwise than as particularly described in the foregoing description and examples.

Example 6

Expression of Recombinant Cytostatin III in CHO Cells

The vector pC1 is used for the expression of Cytostatin III protein. Plasmid pC1 is a derivative of the plasmid pSV2-dhfr [ATCC Accession No. 37146]. Both plasmids contain the mouse DHFR gene under control of the SV40 early promoter. Chinese hamster ovary—or other cells lacking dihydrofolate activity that are transfected with these plasmids can be selected by growing the cells in a selective medium (alpha minus MEM, Lift Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985, 438–4470) plus a fragment isolated from the enhancer of the immediate early gene of human cytomegalovirus (CMV) (Boshart et al., Cell 41:521–530, 1985). Downstream of the promoter are the following single restriction enzyme cleavage sites that allow the integration of the genes: BamHI, Pvull, and Nrul. Behind these cloning sites the plasmid contains translational stop codons in all three reading frames followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosome can also be selected upon co-transfection with a selectable marker such as gpt, G418 or hygromycin. It is advantageous to use more than one selectable marker in the beginning, e.g. G418 plus methotrexate.

The plasmid pC1 is digested with the restriction enzyme BamHI and then dephosphorylated using calf intestinal phosphatase by procedures known in the art. The vector is then isolated from a 1% agarose gel.

The DNA sequence encoding cytostatin III, ATCC #97332, is amplified using PCR oligonucleotide primers corresponding to the 5' and 3' sequences of the gene: The 5' primer has the sequence 5' GC <u>GGA TCC</u> TCC CAA CCT CAC TGG CTA C 3' (SEQ ID NO:9) containing the underlined BamH1 restriction enzyme site followed by 19 bases of the sequence of Cytostatin III of FIG. 1 (SEQ ID NO:1). Inserted into an expression vector, as described below, the 5' end of the amplified fragment encoding human Cytostatin III provides an efficient signal peptide. An efficient signal for initiation of translation in eukaryotic cells, as described by Kozak, M., J. Mol. Biol. 196: 947–950 (1987) is appropriately located in the vector portion of the construct.

The 3' primer has the sequence 5' GC GGT ACC CTA TCT GAC CTT CCT G 3' (SEQ ID NO:10) containing the Asp718 restriction followed by nucleotides complementary to the last 16 nucleotides of the Cytostatin III coding sequence set out in FIG. 1 (SEQ ID NO:1), including the stop codon.

The amplified fragments are isolated from a 1% agarose gel as described above and then digested with the endonuclease BamiHI and then purified again on a 1% agarose gel. The isolated fragment and the dephosphorylated vector aare then ligated with T4 DNA ligase. *E.coli* HB101 cells are then transformed and bacteria identified that contained the plasmid pC1 inserted in the correct orientation using the restriction enzyme BaniHI. The sequence of the inserted gene is confirmed by DNA sequencing.

Transfection of CHO-DHFR-cells

Chinese hamster ovary cells lacking an active DHFR enzyme are used for transfection. 5 mg of the expression plasmid C1 are cotransfected with 0.5 mg of the plasmid pSVneo using the lipofectin method (Felgner et al., supra). The plasmid pSV2-neo contains a dominant selectable marker, the gene neo from Tn5 encoding an enzyme that confers resistance to a group of antibiotics including G418.

The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25, 50 nm, 100 nm, 200 nm, 400 nm). Clones growing at the highest concentrations of methotrexate are then transferred to new 6-well plates containing even higher concentrations of methotrexate (500 nM, 1 mM, 2 mM, 5 mM). The same procedure is repeated until clones grow at a concentration of 100 mM.

The expression of the desired gene product is analyzed by Western blot analysis and SDS-PAGE.

Numerous modifications and variations of the present invention are possible in light of the above teachings and, therefore, are within the scope of the appended claims.

What is claimed is:

1. An isolated antibody or fragment thereof that specifically binds to a protein selected from the group consisting of:
   (a) a protein consisting of a polypeptide fragment of SEQ ID NO:2, wherein said fragment has cytostatin III activity; and
   (b) a protein consisting of amino acid residues 1 to 135 of SEQ ID NO:2.

2. The antibody or fragment thereof of claim 1 that specifically binds protein (a).

3. The antibody or fragment thereof of claim 1 that specifically binds protein (b).

4. The antibody or fragment thereof of claim 2 that specifically binds protein (b).

5. The antibody or fragment thereof of claim 3 wherein said protein bound by said antibody or fragment thereof is glycosylated.

6. The antibody or fragment thereof of claim 3 which is a human antibody.

7. The antibody or fragment thereof of claim 3 which is a polyclonal antibody.

8. The antibody or fragment thereof of claim 3 which is selected from the group consisting of:
   (a) a chimeric antibody;
   (b) a humanized antibody;
   (c) a single chain antibody; and
   (d) a Fab fragment.

9. The antibody or fragment thereof of claim 3 which is labeled.

10. The antibody or fragment thereof of claim 9 wherein the label is selected from the group consisting of:
   (a) an enzyme; and
   (b) a fluorescent label.

11. The antibody or fragment thereof of claim 3 wherein said antibody or fragment thereof specifically binds to said protein in a Western blot.

12. The antibody or fragment thereof of claim 3 wherein said antibody or fragment thereof specifically binds to said protein in an ELISA.

13. An isolated cell that produces the antibody or fragment thereof of claim 3.

14. A hybridoma that produces the antibody or fragment thereof of claim 3.

15. A method of detecting a protein in a biological sample comprising:
   (a) contacting the biological sample with the antibody or fragment thereof of claim 3; and
   (b) detecting the protein in the biological sample.

16. The method of claim 15 wherein the antibody or fragment thereof is a polyclonal antibody.

17. An isolated antibody or fragment thereof obtained from an animal that has been immunized with a protein selected from the group consisting of:
   (a) a protein consisting of a polypeptide fragment of SEQ ID NO:2, wherein said fragment has cytostatin III activity; and
   (b) a protein consisting of amino acid residues 1 to 135 of SEQ ID NO:2, wherein said antibody or fragment thereof specifically binds to said protein.

18. The antibody or fragment thereof of claim 17 obtained from an animal immunized with protein (a).

19. The antibody or fragment thereof of claim 17 obtained from an animal immunized with protein (b).

20. The antibody or fragment thereof of claim 17 which is a monoclonal antibody.

21. The antibody or fragment thereof of claim 17 which is selected from the group consisting of:
   (a) a chimeric antibody;
   (b) a polyclonal antibody;
   (c) a humanized antibody;
   (d) a single chain antibody; and
   (e) a Fab fragment.

22. An isolated monoclonal antibody or fragment thereof that specifically binds to a protein selected from the group consisting of:
   (a) a protein consisting of a polypeptide fragment of SEQ ID NO:2, wherein said fragment has cytostatin III activity; and
   (b) a protein consisting of amino acid residues 1 to 135 of SEQ ID NO:2.

23. The antibody or fragment thereof of claim 22 that specifically binds protein (a).

24. The antibody or fragment thereof of claim 22 that specifically binds protein (b).

25. The antibody or fragment thereof of claim 23 that specifically binds protein (b).

26. The antibody or fragment thereof of claim 24 wherein said protein bound by said antibody or fragment thereof is glycosylated.

27. The antibody or fragment thereof of claim 24 which is a human antibody.

28. The antibody or fragment thereof of claim 24 which is selected from the group consisting of:
   (a) a chimeric antibody;
   (b) a humanized antibody;
   (c) a single chain antibody; and
   (d) a Fab fragment.

29. The antibody or fragment thereof of claim 24 which is labeled.

30. The antibody or fragment thereof of claim 29 wherein the label is selected from the group consisting of:
   (a) an enzyme; and
   (b) a fluorescent label.

31. The antibody or fragment thereof of claim 24 wherein said antibody or fragment thereof specifically binds to said protein in a Western blot.

32. The antibody or fragment thereof of claim 24 wherein said antibody or fragment thereof specifically binds to said protein in an ELISA.

33. An isolated cell that produces the antibody or fragment thereof of claim 24.

34. A hybridoma that produces the antibody or fragment thereof of claim 24.

35. A method of detecting a protein in a biological sample comprising:
   (a) contacting the biological sample with the antibody or fragment thereof of claim 24; and
   (b) detecting the protein in the biological sample.

36. An isolated antibody or fragment thereof that specifically binds to a protein selected from the group consisting of:
   (a) a protein consisting of a fragment of the mature form of the polypeptide encoded by the cDNA contained in ATCC Deposit Number 97332 having cytostatin III activity; and
   (b) a protein consisting of the mature form of the polypeptide encoded by the cDNA contained in ATCC Deposit Number 97332.

37. The antibody or fragment thereof of claim 36 that specifically binds protein (a).

38. The antibody or fragment thereof of claim 36 that specifically binds protein (b).

39. The antibody or fragment thereof of claim 37 that specifically binds protein (b).

40. The antibody or fragment thereof of claim 38 wherein said protein bound by said antibody or fragment thereof is glycosylated.

41. The antibody or fragment thereof of claim 38 which is a human antibody.

42. The antibody or fragment thereof of claim 38 which is a polyclonal antibody.

43. The antibody or fragment thereof of claim 38 which is selected from the group consisting of:
   (a) a chimeric antibody;
   (b) a humanized antibody;
   (c) a single chain antibody; and
   (d) a Fab fragment.

44. The antibody or fragment thereof of claim 38 which is labeled.

45. The antibody or fragment thereof of claim 44 wherein the label is selected from the group consisting of:
   (a) an enzyme; and
   (b) a fluorescent label.

46. The antibody or fragment thereof of claim 38 wherein said antibody or fragment thereof specifically binds to said protein in a Western blot.

47. The antibody or fragment thereof of claim 38 wherein said antibody or fragment thereof specifically binds to said protein in an ELISA.

48. An isolated cell that produces the antibody or fragment thereof of claim 38.

49. A hybridoma that produces the antibody or fragment thereof of claim 38.

50. A method of detecting a protein in a biological sample comprising:
   (a) contacting the biological sample with the antibody or fragment thereof of claim 38; and
   (b) detecting the protein in the biological sample.

51. The method of claim 50 wherein the antibody or fragment thereof is a polyclonal antibody.

52. An isolated antibody or fragment thereof obtained from an animal that has been immunized with a protein selected from the group consisting of:
   (a) a protein consisting of a fragment of the mature form of the polypeptide encoded by the cDNA contained in ATCC Deposit Number 97332 having cytostatin III activity; and (b) a protein consisting of the mature form of the polypeptide encoded by the cDNA contained in ATCC Deposit Number 97332;
   wherein said antibody or fragment thereof specifically binds to said protein.

53. The antibody or fragment thereof of claim 52 obtained from an animal immunized with protein (a).

54. The antibody or fragment thereof of claim 52 obtained from an animal immunized with protein (b).

55. The antibody or fragment thereof of claim 52 which is a monoclonal antibody.

56. The antibody or fragment thereof of claim 52 which is selected from the group consisting of:
   (a) a chimeric antibody;
   (b) a polyclonal antibody;
   (c) a humanized antibody;
   (d) a single chain antibody; and
   (e) a Fab fragment.

57. An isolated monoclonal antibody or fragment thereof that specifically binds to a protein selected from the group consisting of:
   (a) a protein consisting of a fragment of the mature form of the polypeptide encoded by the cDNA contained in ATCC Deposit Number 97332 having cytostatin III activity; and
   (b) a protein consisting of the mature form of the polypeptide encoded by the cDNA contained in ATCC Deposit Number 97332.

58. The antibody or fragment thereof of claim 57 that specifically binds protein (a).

59. The antibody or fragment thereof of claim 57 that specifically binds protein (b).

60. The antibody or fragment thereof of claim 58 that specifically binds protein (b).

61. The antibody or fragment thereof of claim 59 wherein said protein bound by said antibody or fragment thereof is glycosylated.

62. The antibody or fragment thereof of claim 59 which is a human antibody.

63. The antibody or fragment thereof of claim 59 which is selected from the group consisting of:
   (a) a chimeric antibody;
   (b) a humanized antibody;
   (c) a single chain antibody; and
   (d) a Fab fragment.

64. The antibody or fragment thereof of claim 59 which is labeled.

65. The antibody or fragment thereof of claim 64 wherein the label is selected from the group consisting of:
   (a) an enzyme; and
   (b) a fluorescent label.

66. The antibody or fragment thereof of claim 59 wherein said antibody or fragment thereof specifically binds to said protein in a Western blot.

67. The antibody or fragment thereof of claim 59 wherein said antibody or fragment thereof specifically binds to said protein in an ELISA.

68. An isolated cell that produces the antibody or fragment thereof of claim 59.

69. A hybridoma that produces the antibody or fragment thereof of claim 59.

70. A method of detecting a protein in a biological sample comprising:
   (a) contacting the biological sample with the antibody or fragment thereof of claim 59; and
   (b) detecting the protein in the biological sample.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 944 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 94..498

(xi) SEQUENCE DESCRIPTION: SEQ ID NO:1:

```
CACGAGCTGG AATCTCTCAG CCTCACCTGC CAGACAACAC CCCCTCCTTC CTCACCCTGT    60

CTCCTGCATT CTCCTGAAAC CTTCATCCAC ACA ATG CCT CCC AAC CTC ACT GGC   114
                                    Met Pro Pro Asn Leu Thr Gly
                                      1               5

TAC TAC CGC TTT GTC TCG CAG AAG AAC ATG GAG GAC TAC CTG CAA GCC   162
Tyr Tyr Arg Phe Val Ser Gln Lys Asn Met Glu Asp Tyr Leu Gln Ala
         10                  15                  20

CTA AAC ATC AGC TTG GCT GTG CGG AAG ATC GCG CTG CTG CTG AAG CCG   210
Leu Asn Ile Ser Leu Ala Val Arg Lys Ile Ala Leu Leu Leu Lys Pro
 25                  30                  35

GAC AAG GAG ATC GAA CAC CAG GGC AAC CAC ATG ACG GTG AGG ACG CTC   258
Asp Lys Glu Ile Glu His Gln Gly Asn His Met Thr Val Arg Thr Leu
 40                  45                  50                  55

AGC ACC TTC CGA AAC TAC ACT TTG CAG TTT GAT GTG GGA GTG GAG TTT   306
Ser Thr Phe Arg Asn Tyr Thr Leu Gln Phe Asp Val Gly Val Glu Phe
                 60                  65                  70

GAG GAG GAC CTC AGG AGC GTG GAC GGA CGA AAA TGC CAG ACC ATA GTA   354
Glu Glu Asp Leu Arg Ser Val Asp Gly Arg Lys Cys Gln Thr Ile Val
         75                  80                  85

ACC TGG GAG GAG GAG CAC CTG GTG TGT GTG CAG AAA GGG GAG GTC CCC   402
Thr Trp Glu Glu Glu His Leu Val Cys Val Gln Lys Gly Glu Val Pro
             90                  95                 100

AAC CGG GGC TGG AGA CAC TGG CTG GAG GGA GAG ATG CTG TAT CTG GAA   450
Asn Arg Gly Trp Arg His Trp Leu Glu Gly Glu Met Leu Tyr Leu Glu
        105                 110                 115

CTG ACT GCA AGG GAT GCA GTG TGC GAG CAG GTC TTC AGG AAG GTC AGA   498
Leu Thr Ala Arg Asp Ala Val Cys Glu Gln Val Phe Arg Lys Val Arg
120                 125                 130                 135

TAGCCGGAGA GGAGCCAAGA TCCCTCCAGA CAGCACCAGC TCACAGACGC TCTTGTTGTG   558

CCCCCTTCAA GCCCAGATTG TGCCAGGTCA GCTGTCCCTT CCTCTGGCCA CCTTTCCTCC   618
```

```
CTCTGGGTCC CTCCTCACCC CTCCCCGTGT TAATCTGTAA CTTGGAGCCC CCAGGACAAA       678

GTCCTTTCTC ACACTCCACT GCCCAATAGT GACCTCACTT CCAGGTCAAG GTCTGGCGTC       738

CCAAATGAAA GAAGCAGGCA AAGGGAAGGA GCCCCTGAGG ACAACCAATC TCCGCTCTCT       798

CCTGTCCATT TGACCTCTTC TTTTCCTTCT AAGAAAGAAC TAAGCTTTGG GCATTTGGCG       858

ATTAGTGAAA ATTCTATCCT GATGGACTTC TGGAAAACTG TGACTGGGGT TCAACAGTTT       918

AAACAGGGGC TACTGGGGGA AAAAA                                            944
```

(2) INFORMATION FOR SEQ ID NO:2:

(i) SEQUENCE CHARACTERISTICS:
        (A) LENGTH: 135 amino acids
        (B) TYPE: amino acid
        (D) TOPOLOGY: linear (ii) MOLECULE TYPE: protein (xi) SEQUENCE DESCRIPTION: SEQ ID NO:2:

```
Met Pro Pro Asn Leu Thr Gly Tyr Tyr Arg Phe Val Ser Gln Lys Asn
 1               5                  10                  15

Met Glu Asp Tyr Leu Gln Ala Leu Asn Ile Ser Leu Ala Val Arg Lys
             20                  25                  30

Ile Ala Leu Leu Leu Lys Pro Asp Lys Glu Ile Glu His Gln Gly Asn
         35                  40                  45

His Met Thr Val Arg Thr Leu Ser Thr Phe Arg Asn Tyr Thr Leu Gln
     50                  55                  60

Phe Asp Val Gly Val Glu Phe Glu Glu Asp Leu Arg Ser Val Asp Gly
 65                  70                  75                  80

Arg Lys Cys Gln Thr Ile Val Thr Trp Glu Glu His Leu Val Cys
                 85                  90                  95

Val Gln Lys Gly Glu Val Pro Asn Arg Gly Trp Arg His Trp Leu Glu
            100                 105                 110

Gly Glu Met Leu Tyr Leu Glu Leu Thr Ala Arg Asp Ala Val Cys Glu
            115                 120                 125

Gln Val Phe Arg Lys Val Arg
            130                 135
```

(2) INFORMATION FOR SEQ ID NO:3:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CGCGCATGCC TCCCAACCTC AC                                                22
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GCGAAGCTTC TATCTGACCT TCCTG                                            25

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GCGGATCCAC CATGCCTCCC AACCTCACT                                        29

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGGTACCCT ATCTGACCTT CCTG                                             24

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCGGATCCAC CATGCCTCCC AACCTCACT                                        29

(2) INFORMATION FOR SEQ ID NO:8:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCTCTAGATC AAGCGTAGTC TGGGACGTCG TATGGGTATC TGACCTTCCT GAA             53

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCGGATCCTC CCAACCTCAC TGGCTAC                                          27

(2) INFORMATION FOR SEQ ID NO:10:
```

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GCGGTACCCT ATCTGACCTT CCTG                                              24

(2) INFORMATION FOR SEQ ID NO:11:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Met Ala Asp Ala Phe Val Gly Thr Trp Lys Leu Val Asp Ser Lys Asn
    1               5                  10                  15

Phe Asp Asp Tyr Met Lys Ser Leu Gly Val Gly Phe Ala Thr Arg Gln
                20                  25                  30

Val Ala Ser Met Thr Lys Pro Thr Thr Ile Ile Glu Lys Asn Gly Asp
                35                  40                  45

Thr Ile Thr Ile Lys Thr Gln Ser Thr Phe Lys Asn Thr Glu Ile Asn
        50                  55                  60

Phe Gln Leu Gly Ile Glu Phe Asp Glu Val Thr Ala Asp Asp Arg Lys
    65                  70                  75                  80

Val Lys Ser Leu Val Thr Leu Asp Gly Gly Lys Leu Ile His Val Gln
                    85                  90                  95

Lys Trp Asn Gly Gln Glu Thr Thr Leu Thr Arg Glu Leu Val Asp Gly
                    100                 105                 110

Lys Leu Ile Leu Thr Leu Thr His Gly Ser Val Val Ser Thr Arg Thr
                    115                 120                 125

Tyr Glu Lys Glu Ala
            130

(2) INFORMATION FOR SEQ ID NO:12:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Met Val Asp Ala Phe Val Gly Thr Trp Lys Leu Val Asp Ser Lys Asn
    1               5                  10                  15

Phe Asp Asp Tyr Met Lys Ser Leu Gly Val Gly Phe Ala Thr Arg Gln
                20                  25                  30

Val Gly Asn Met Thr Lys Pro Thr Thr Ile Ile Glu Val Asn Gly Asp
                35                  40                  45

Thr Val Ile Ile Lys Thr Gln Ser Thr Phe Lys Asn Thr Glu Ile Ser
        50                  55                  60

Phe Lys Leu Gly Val Glu Phe Asp Glu Thr Thr Ala Asp Asp Arg Lys

```
                65                   70                  75                  80
         Val Lys Ser Ile Val Thr Leu Asp Gly Gly Lys Leu Val His Val Gln
                         85                  90                  95

Lys Trp Asn Gly Gln Glu Thr Ser Leu Val Arg Glu Met Val Asp Gly
                         100                 105                 110

Lys Leu Ile Leu Thr Leu Thr His Gly Thr Ala Val Cys Thr Arg Thr
                         115                 120                 125

Tyr Glu Lys Gln Ala
                 130

(2) INFORMATION FOR SEQ ID NO:13:

(i) SEQUENCE CHARACTERISTICS:
        (A) LENGTH: 133 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Val Asp Ala Phe Leu Gly Thr Trp Lys Leu Val Asp Ser Lys Asn
    1               5                   10                  15

Phe Asp Asp Tyr Met Lys Ser Leu Gly Val Gly Phe Ala Thr Arg Gln
                    20                  25                  30

Val Ala Ser Met Thr Lys Pro Thr Thr Ile Ile Glu Lys Asn Gly Asp
                    35                  40                  45

Ile Leu Thr Leu Lys Thr His Ser Thr Phe Lys Asn Thr Glu Ile Ser
                50                  55                  60

Phe Lys Leu Gly Val Glu Phe Asp Glu Thr Thr Ala Asp Asp Arg Lys
    65                  70                  75                  80

Val Lys Ser Ile Val Thr Leu Asp Gly Gly Lys Leu Val His Leu Gln
                    85                  90                  95

Lys Trp Asp Gly Gln Glu Thr Thr Leu Val Arg Glu Leu Ile Asp Gly
                    100                 105                 110

Lys Leu Ile Leu Thr Leu Thr His Gly Thr Ala Val Cys Thr Arg Thr
                    115                 120                 125

Tyr Glu Lys Glu Ala
            130

(2) INFORMATION FOR SEQ ID NO:14:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Met Pro Pro Asn Leu Thr Gly Tyr Tyr Arg Phe Val Ser Gln Lys Asn
    1               5                   10                  15

Met Glu Asp Tyr Leu Gln Ala Leu Asn Ile Ser Leu Ala Val Arg Lys
                    20                  25                  30

Ile Ala Leu Leu Lys Pro Asp Lys Glu Ile Glu His Gln Gly Asn His
                    35                  40                  45

Met Thr Val Arg Thr Leu Ser Thr Phe Arg Asn Tyr Thr Leu Gln Phe
                50                  55                  60
```

-continued

```
Asp Val Gly Val Gln Lys Gly Glu Val Pro Asn Arg Gly Trp Arg His
65                  70                  75                  80

Trp Leu Glu Gly Glu Leu Leu Tyr Leu Glu Leu Thr Ala Arg Asp Ala
                85                  90                  95

Val Cys Glu Gln Val Phe Arg Lys Val Arg
                100             105
```

(2) INFORMATION FOR SEQ ID NO:15:

(i) SEQUENCE CHARACTERISTICS:
      (A) LENGTH: 131 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:15:

```
Met Val Glu Ala Phe Cys Ala Thr Trp Lys Leu Thr Asn Ser Gln Asn
1               5                   10                  15

Phe Asp Glu Tyr Met Lys Ala Leu Gly Val Gly Phe Ala Thr Arg Gln
                20                  25                  30

Val Gly Asn Val Thr Lys Pro Thr Val Ile Ile Ser Gln Glu Gly Asp
            35                  40                  45

Lys Val Val Ile Arg Thr Leu Ser Thr Phe Lys Asn Thr Glu Ile Ser
50                  55                  60

Phe Gln Leu Gly Glu Phe Asp Glu Thr Thr Ala Asp Asp Arg Asn Cys
65                  70                  75                  80

Lys Ser Val Val Ser Leu Asp Gly Asp Lys Leu Val His Ile Gln Lys
                85                  90                  95

Trp Asp Gly Lys Glu Thr Asn Phe Val Arg Glu Ile Lys Asp Gly Lys
                100                 105                 110

Met Val Met Thr Leu Thr Phe Gly Asp Val Val Ala Val Arg His Tyr
            115                 120                 125

Glu Lys Ala
        130
```